US008147837B2

(12) United States Patent
Bercovier et al.

(10) Patent No.: US 8,147,837 B2
(45) Date of Patent: Apr. 3, 2012

(54) USE OF MYCOBACTERIAL MANNOSYLATED LIPOGLYCANS PEPTIDE MIMOTOPES FOR TREATING INFLAMMATION

(75) Inventors: Herve Bercovier, Jerusalem (IL); Ayelet Barenholz, Jerusalem (IL)

(73) Assignee: Yissum Research Development Company of The Hebrew University of Jerusalem, Jerusalem (IL)

( * ) Notice: Subject to any disclaimer, the term of this patent is extended or adjusted under 35 U.S.C. 154(b) by 912 days.

(21) Appl. No.: 11/630,115

(22) PCT Filed: Jun. 23, 2005

(86) PCT No.: PCT/IL2005/000674
§ 371 (c)(1),
(2), (4) Date: Dec. 20, 2006

(87) PCT Pub. No.: WO2006/001011
PCT Pub. Date: Jan. 5, 2006

(65) Prior Publication Data
US 2008/0318868 A1     Dec. 25, 2008

Related U.S. Application Data

(60) Provisional application No. 60/582,221, filed on Jun. 24, 2004.

(51) Int. Cl.
*A61K 39/00* (2006.01)
(52) U.S. Cl. .................................. 424/185.1; 424/184.1
(58) Field of Classification Search ................. 424/185.1
See application file for complete search history.

(56) References Cited

U.S. PATENT DOCUMENTS

| 6,699,703 B1 * | 3/2004 | Doucette-Stamm et al. ................. 435/252.3 |
| 7,273,721 B2 | 9/2007 | Pompejus et al. |

FOREIGN PATENT DOCUMENTS

| WO | 93/18150 A1 | 9/1993 |
| WO | WO 93/18150 * | 9/1993 |
| WO | 03/049752 A2 | 6/2003 |

OTHER PUBLICATIONS

Hamasur et al 1999 Vaccine vol. 17 Issue 22 pp. 2853-2861.*
Greenspan et al. (Nature Biotechnology 7: 936-937, 1999).*
Nigou, et al., "Mannosylated Lipoarabinomannans Inhibit IL-12 Production by Human Dendritic Cells: Evidence for a Negative Signal Delivered Through the Mannose Receptor", The Journal of Immunology, vol. 166, pp. 7477-7485, (2001).
Nigou, et al., "Mycobacterial lipoarabinomannans: modulators of dendritic cell function and the apoptotic response", Microbes and Infection, vol. 4, pp. 945-953, (2002).
Olson, et al., "Design and Synthesis of a Protein β-Turn Mimetic", J. Am. Chem. Soc., vol. 112, pp. 323-333, (1990).
Pincus, et al., "Peptides That Mimic the Group B Streptococcal Type III Capsular Polysaccharide Antigen", The Journal of Immunology, vol. 160, pp. 293-298, (1998).
Prinzis, et al., "Structure and anitgenicity of lipoarabinomannan from *Mycobacterium bovis* BCG", Journal of General Microbiology, vol. 139, pp. 2649-2658, (1993).
Quesniaux, et al., "Toll-Like Receptor 2 (TLR2)-Dependent-Positive and TLR2-Independent-Negative Regulation of Proinflammatory Cytokines by Mycobacterial Lipomannans", The Journal of Immunology, vol. 172, pp. 4425-4434, (2004).
Schlesinger, et al., "Binding of the Terminal Mannosyl Units of Lipoarabinomannan from a Virulent Strain of Mycobacterium Tuberculosis to Human Macrophages", Journal of Immunology, vol. 152, pp. 4070-4079, (1994).
Sethi, et al., "Contraction-Mediated Pinocytosis of RGD-Peptide by Dermal Fibroblasts: Inhibition of Matrix Attachment Blocks Contraction and Disrupts Microfilament Organisation", Cell Motility and Cytoskeleton, vol. 52, pp. 231-241, (2002).
Shirakawa, et al., "The Inverse Association Between Tuberculin Responses and Atopic Disorder", Science, vol. 275, pp. 77-79, (1997).
Shirtcliffe, et al., "An inverse correlation between estimated tuberculosis notification rates and asthma symptoms", Respirology, vol. 7, pp. 153-155, (2002).
Singh, et al., "Advances in Vaccine Adjuvants for Infectious Diseases", Current HIV Research, vol. 1, pp. 309-320, (2003).
Smith, et al., "Libraries of Peptides and Proteins Displayed on Filamentous Phage", Methods in Enzymology, vol. 217, pp. 228-257, (1993).
Stern, et al., "Helical epitopes determined by low-stringency antibody screening of a combinatorial peptide library", FASEB J., vol. 11, pp. 147-153, (1997).

(Continued)

*Primary Examiner* — Gary Nickol
*Assistant Examiner* — Nina Archie
(74) *Attorney, Agent, or Firm* — Susanne M. Hopkins; Ari G. Zytcer

(57) ABSTRACT

The present invention is based on the discovery that biological peptide-based mimotopes of mannose-containing cell-wall compounds of *Mycobacterium tuberculosis*, specifically, ManLAM, have an anti-inflammatory effect and immunoregulator effect in animal models of inflammation. Such models include animal models of allergic peritonitis, allergic asthma and septic shock model (mice injected with LPS) and in Crohn's disease model (TNBS-induced colitis). Thus, the present invention concerns the use a molecule, particularly, an amino acid based molecule for the production of a pharmaceutical composition for the treatment of an inflammatory condition, the amino acid comprising one or more peptides characterized in that it can bind to ManLAM binding antibodies; and/or it can elicit an immune response in a subject inoculated therewith, giving rise to production of ManLAM-binding antibodies. The invention also provides pharmaceutical compositions for treating inflammatory conditions and comprising the amino acid-based molecule, as well as to methods of treatment of such conditions by administering to a subject an amount of the amino-acid based molecules.

2 Claims, 9 Drawing Sheets

OTHER PUBLICATIONS

Temkin, et al., "Tumor necrosis factors in a murine model of allergic peritonitis: effects on eosinophil accumulation and inflammatory mediators' release", Cytokine, vol. 24, pp. 74-80, (2003).

Tibbetts, et al., "Linear and cyclic LFA-1 and ICAM-1 peptides inhibit T cell adhesion and function", Peptides, vol. 21, pp. 1161-1167, (2000).

Valadon, et al., "Enhancement of ELISAs for screening peptides in epitope phage display libraries", Journal of Immunological Methods, vol. 197, pp. 171-179, (1996).

Von Mutius, et al., "International patterns of tuberculosis and the prevalence of symptoms of asthma, rhinitis, and eczema", Thorax, vol. 55, pp. 449-453, (2000).

Vyas, et al., "Structural basis of peptide-carbohydrate mimicry in an antibody-combining site", PNAS, vol. 100, No. 25, pp. 15023-15028, (2003).

Wang, et al., "Epitope Identification and Discovery Using Phage Display Libraries: Applications in Vaccine Development and Diagnostics", Current Drug Targets, vol. 5, pp. 1-15, (2004).

Wu, et al., "The Pharmacological Actions of Nicotine on the Gastrointestinal Tract", Journal of Pharmacological Sciences, vol. 94, pp. 348-358, (2004).

Yoshimura, et al., "Role of NFκB in antigen presentation and development of regulatory T cells elucidated by treatment of dendritic cells with the proteasome inhibitor PSI", Eur. J. Immunol., vol. 31, pp. 1883-1893, (2001).

Zabrocki, et al., "Conformational Mimicry. 1. 1,5-Disubstituted Tetrazole Ring as a Surrogate for the Cis Amide Bond", J. Am. Chem. Soc., vol. 110, pp. 5875-5880, (1988).

Zechel, et al., "Synthetic glucagon antagonists and partial agonists", Int. J. Peptide Protein Res., vol. 38, pp. 131-138, (1991).

Zuany-Amorim, et al., "Suppression of airway eosinophilia by killed mycobacerium vaccae-induced allergen-specific regulatory T-cells", Nature Medicine, vol. 8, No. 6, pp. 625-629, (2002).

Miyakk, et al., "1,2,3,4-Tetrahydroisoquinoline-3-carboxylic Acid Angiotensin: Synthesis and Angiotensin Converting Enzyme Inhibitory Activity of 1,2,3,4-Tetrahydroisoquinoline-3-carboxylic Acid Derivatives", J. Takeda Res. Labs., vol. 43, pp. 53-76, (1984).

DeLuca, et al., "Parenteral Drug-Delivery Systems", Pharmaceutics and Pharmacy Practice, ch. 8, pp. 238-250, J.B. Lippincott Co., Philadelphia, Pa., Banker and Chalmers, eds., (1982).

Trissel, "Intravenous Infusion Solutions", ASHP Handbook on Injectable Drugs, 4th ed., pp. 622-630, (1986).

Enshell-Seijffers, et al., "Phage Display Selection and Analysis of Ab-Binding Epitopes", Current Protocols in Immunology, vol. 2, pp. 9.8.1-9.8.27, (2002).

Abad, et al., "Therapeutic Effects of Vasoactive Intestinal Peptide in the Trinitrobenzene Sulfonic Acid Mice Model of Crohn's Disease", Gastroenterology, vol. 124, pp. 961-971, (2003).

Antunes, et al., "Serological screening for tuberculosis in the community: an evaluation of the Mycodot procedure in an African population with high HIV-2 prevalence (Republic of Guinea-Bissau)", Research in Microbiology, vol. 153, pp. 301-305, (2002).

Agrawal, et al., "Novel immunomodulatory oligonucleotides prevent development of allergic airway inflammation and airway hyperresponsiveness in asthma", International Immunopharmacology, vol. 4, pp. 127-138, (2004).

Arnold, et al., "Chimeric Rhinoviruses as Tools for Vaccine Development and Characterization of Protein Epitopes", Intervirology, vol. 39, pp. 72-78, (1996).

Barenholz, et al., "A peptide mimetic of the mycobacterial mannosylated lipoarabinomannan: characterization and potential applications", Journal of Medical Microbiology, vol. 56, pp. 579-586, (2007).

Barnes, et al., "Cytokine Production Induced by *Mycobacterium tuberculosis* Lipoarabinomannan", The Journal of Immunology, vol. 149, No. 2, pp. 541-547, (1992).

Benhar, "Biotechnological applications of phage and cell display", Biotechnology Advances, vol. 19, pp. 1-33, (2001).

Blyth, et al., "Lung inflammation and epithelial changes in a murine model of atopic asthma", Am. J. Respir. Cell Mol. Biol., vol. 14, pp. 425-438, (1996).

Chatterjee, et al. "Lipoarabinomannan of *Mycobacterium tuberculosis*: Capping with Mannosyl Residues in Some Strains", The Journal of Biological Chemistry, vol. 267, No. 9, pp. 6234-6239, (1992).

Ciesielski, "BCG Vaccination and the PPD test: what the clinician needs to know", J Fam Pract, vol. 40, pp. 76-80, Abstract, (1995).

Dao, et al., "*Mycobacterium tuberculosis* Lipomannan Induces Apoptosis and Interleukin-12 Production in Macrophages", Infection and Immunity, vol. 72, No. 4, pp. 2067-2074, (2004).

D'Argenio, et al., "Expression of apoptosis-related proteins in rat with induced colitis", Int J Colorectal Dis, vol. 19, pp. 451-490, (2004).

Dimaio, et al., "Synthesis of Chiral Piperazin-2-ones as Model Peptidomimetics", J. Chem. Soc. Perkin Trans. I, pp. 1687-1689, (1989).

Enshell-Seijffers, et al., "The Mapping and Reconstitution of a Conformational Discontinuous B-cell Epitope of HIV-1", J. Mol. Biol., vol. 334, pp. 87-101, (2003).

Garvey, et al., "3,4-Disubstituted γ-Lactam Rings as Conformationally Constrained Mimics of Peptide Derivatives Containing Aspartic Acid or Norleucine", J. Org. Chem., vol. 55, pp. 936-940, (1990).

Glatman-Freedman, "Advances in antibody-mediated immunity against *Mycobacterium tuberculosis*: implications for a novel vaccine strategy", FEMS Immunology and Medical Microbiology, vol. 39, pp. 9-16, (2003).

Greenspan, et al., "Defining epitopes: It's not as easy as it seems", Nature Biotechnology, vol. 17, pp. 836-837, (1999).

Grimaldi, et al., "Depletion of eosinophils in mice through the use of antibodies specific for C-C chemokine receptor 3 (CCR3)", Journal of Leukocyte Biology, vol. 65, pp. 846-853, (1999).

Guérardel, et al., "Structural Study of Lipomannan and Lipoarabinomannan from *Mycobacterium chelonae*", The Journal of Biological Chemistry, vol. 277, No. 34, pp. 30635-30648, (2002).

Hamasur, et al., "*Mycobacterium tuberculosis* arabinomannan-protein conjugates protect against tuberculosis", Vaccine, vol. 21, pp. 4081-4093, (2003).

Hamasur, et al., "Synthesis and immunologic characterisation of *Mycobacterium tuberculosis* lipoarabinomannan specific oligosaccharide-protein conjugates", Vaccine, vol. 17, pp. 2853-2861, (1999).

Hamasur, et al., "Rapid diagnosis of tuberculosis by detection of mycobacterial lipoarabinomannan in urine", Journal of Microbiological Methods, vol. 45, pp. 41-52, (2001).

Harlow, et al., "Antibodies—a laboratory manual", ch. 5, p. 76, (1988).

Hetland, et al., "Involvement of Antilipoarabinomannan Antibodies in Classical Complement Activation in Tuberculosis", Clinical and Diagnostic Laboratory Immunology, vol. 5, No. 2, pp. 211-218, (1998).

Hubeau, et al., "Extended freeze-dried *Mycobacterium bovis* Bacillus Calmette-Guérin induces the release of interleukin-12 but not tumour necrosis factor-α by alveolar macrophages, both in vitro and in vivo", Clin Exp Allergy, vol. 33, pp. 386-393, (2003).

Jacobson, et al., "The pneumococcal conjugate vaccine", Minerva Pediatr., vol. 54, pp. 295-303, Abstract, (2002).

Jining, et al., "Design, structure and biological activity of β-turn peptides of CD2 protein for inhibition of T-cell adhesion", Eur. J. Biochem., vol. 271, pp. 2873-2886, (2004).

Jones, et al., "Amide Bond Isosteres: Imidazolines in Pseudopeptide Chemistry", Tetrahedron Letters, vol. 29, No. 31, pp. 3853-3856, (1988).

Kahn, et al., "The Incorporation of β-Turn Prosthetic Units into Merrifield Solid Phase Peptide Synthesis", Tetrahedron Letters, vol. 30, No. 18, pp. 2317-2320, (1989).

Kaur, et al., "Characterization of the epitope of anti-lipoarabinomannan antibodies as the terminal hexaarabinofuranosyl motif of mycobacterial arabinans", Microbiology, vol. 148, pp. 3049-3057, (2002).

Kazmierski, et al., "Topographic Design of Peptide Neurotransmitters and Hormones on Stable Backbone Templates: Relation of Conformation and Dynamics to Bioactivity", J. Am. Chem. Soc., vol. 113, pp. 2275-2283, (1991).

Kazmierski, et al., "Asymmetric Synthesis of Topographically Constrained Amino Acids: Synthesis of the Optically Pure Isomers of α,β-Dimethyl-Phenylalamine and α,β-Dimethyl-1,2,3,4-

Tetrahydroisoquinoline-3-Carboxylic Acid", Tetrahedron Letters, vol. 32, No. 41, pp. 5769-5772, (1991).

Kemp, et al., "Conformationally Restricted Cyclic Nonapeptides Derived from L-Cysteine and LL-3-Amino-2-piperidone-6-carboxylic Acid (LL-Acp), a Potent β-Turn-Inducing Dipeptide Analogue", J. Org. Chem., vol. 50, pp. 5834-5838, (1985).

Kemp, et al., "(2S,5S,8S,11S)-1-Acetyl-1,4-Diaza-3-Keto-5-Carboxy-10-Thia-Tricyclo-[2.8.04,8]-Tridecane, 1 the Preferred Conformation of 1 (1 ≡ αTemp-OH) and its Peptide Conjugates αTemp-L-(Ala)n-OR (n=1 to 4) and α-temp-L-Ala-L-Phe-L-Lys(εBoc)-L-LYS(ε-Boc)-NHMe Studies of Templates for α-Helix Formation", Tetrahedron Letters, vol. 29, No. 39, pp. 4935-4938, (1988).

Kemp, et al., "A Convenient Preparation of Derivatives of 3(S)-Amino-10(R)-Carboxy-1,6-Diaza-Cyclodeca-2,7-Dione the Dilactam of L-α,γ-Diaminobutyric Acid and D-Glutamic Acid: a β-Turn Template", Tetrahedron Letters, vol. 29, No. 40, pp. 5057-5060, (1988).

Kemp, et al., "Conformational Analysis of Peptide-Functionalized Diacylaminoepindolidiones 1H NMR Evidence for β-Sheet Formation", Tetrahedron Letters, vol. 29, No. 40, pp. 5081-5082, (1988).

Kemp, et al., "Amino Acid Derivatives That Stabilize Secondary Structures of Polypeptides. 4. Practical Synthesis of 4-(Alkylamino)-3-cyano-6-azabicyclo[3.2.1]oct-3-enes (Ben Derivatives) as γ-Turn Templates", J. Org. Chem., vol. 54, pp. 109-115, (1989).

Kibbelaar, et al., "Expression of the Embryonal Neural Cell Adhesion Molecule N-Cam in Lung Carcinoma. Diagnostic Usefulness of Monoclonal Antibody 735 for the Distinction Between Small Cell Lung Cancer and Non-Small Cell Lung Cancer", Journal of Pathology, vol. 159, pp. 23-28, (1989).

Leech, et al., "Regulation of p53 by Macrophage Migration Inhibitory Factor in Inflammatory Arthritis", Arthritis & Rheumatism, vol. 48, No. 7, pp. 1881-1889, (2003).

Locke, et al., "Comparison of Airway Remodeling in Acute, Subacute, and Chronic Models of Allergic Airways Disease", Am J Respir Cell Mol Biol, vol. 36, pp. 625-632, (2007).

Luo, et al., "A Molecular Basis for Functional Peptide Mimicry of a Carbohydrate Antigen", The Journal of Biological Chemistry, vol. 275, No. 21, pp. 16146-16154, (2000).

Maeda, et al., "The Cell Surface Receptor DC-SIGN Discriminates between Mycobacterium Species through Selective Recognition of the Mannose Caps on Lipoarabinomannan", The Journal of Biological Chemistry, vol. 278, No. 8, pp. 5513-5516, (2003).

Maekura, et al., "Clinical Evaluation of Anti-Tuberculous Glycolipid Immunoglobulin G Antibody Assay for Rapid Serodiagnosis of Pulmonary Tuberculosis", Journal of Clinical Microbiology, vol. 39, No. 10, pp. 3603-3608, (2001).

Martin, et al., "T cell cytokines: animal models", Paediatric respiratory reviews, vol. 5, suppl A, pp. S47-S51, (2004).

Meloen, et al., "Review: Mimotopes: realization of an unlikely concept", Journal of Molecular Recognition, vol. 13, pp. 352-359, (2000).

Mukherjee, et al., "Protective Murine Monoclonal Antibodies to *Cryptococcus neoformans*", Infection and Immunity, vol. 60, No. 11, pp. 4534-4541, (1992).

Nagai, et al., "Synthesis of a Bicyclic Dipeptide with the Shape of β-Turn Central Part", Tetrahedron Letters, vol. 26, No. 5, pp. 647-650, (1985).

Navoa, et al., "Specificity and Diversity of Antibodies to *Mycobacterium tuberculosis* Arabinomannan", Clinical and Diagnostic Laboratory Immunology, vol. 10, No. 1, pp. 88-94, (2003).

Neurath, et al., "Antibodies to Interleukin 12 Abrogate Established Experimental Colitis in Mice", The Journal of Experimental Medicine, vol. 182, pp. 1281-1290, (1995).

Nguyen, et al., "Involvement of macrophage mannose receptor in the binding and transmission of HIV by macrophages", Eur. J. Immunol., vol. 33, pp. 483-493, (2003).

* cited by examiner

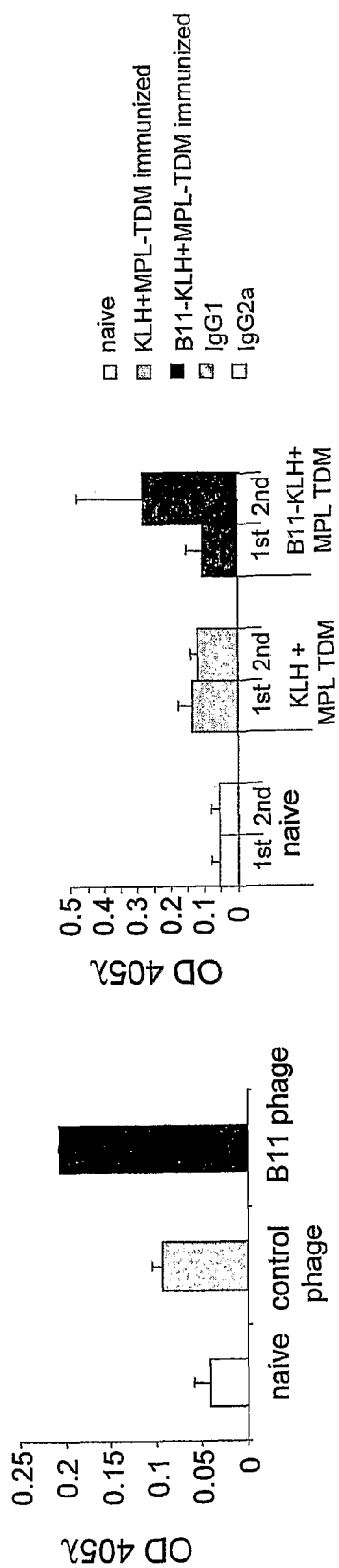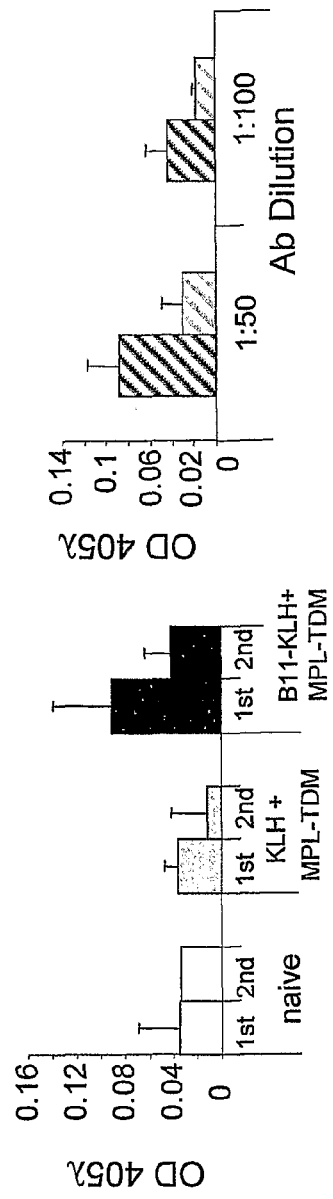

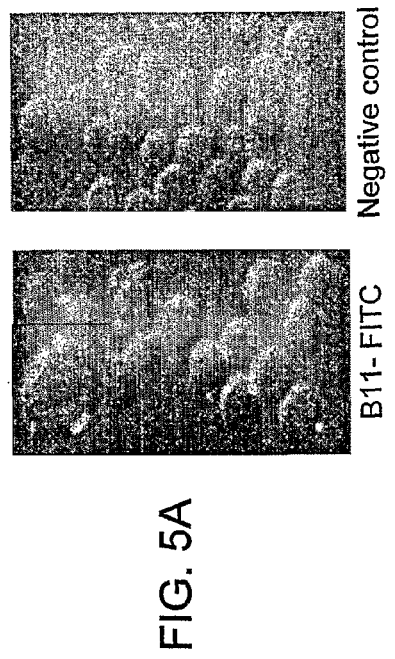
FIG. 5A
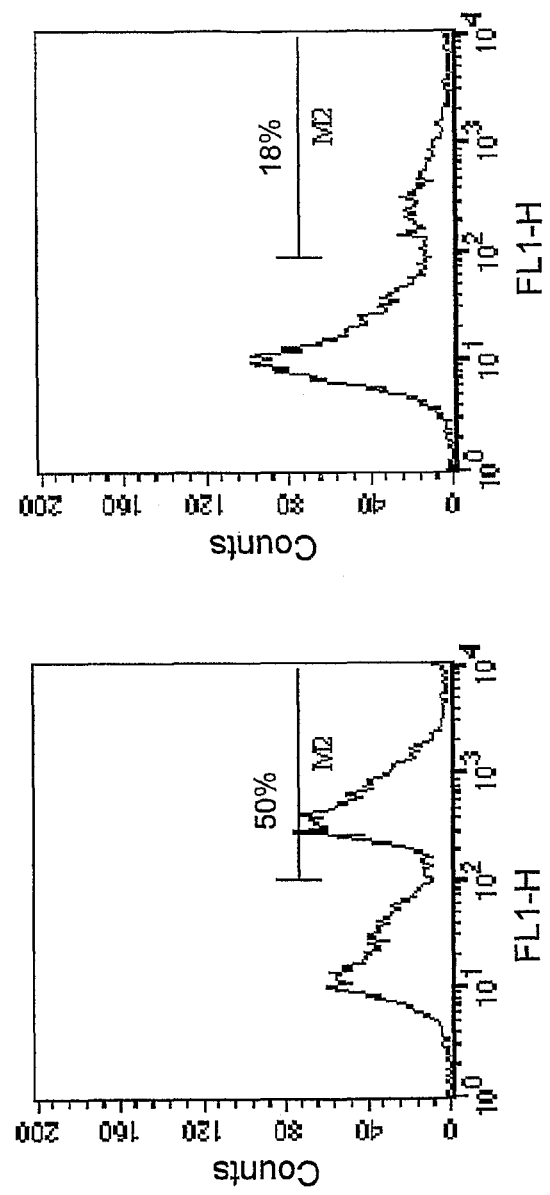
FIG. 5B
FIG. 5C

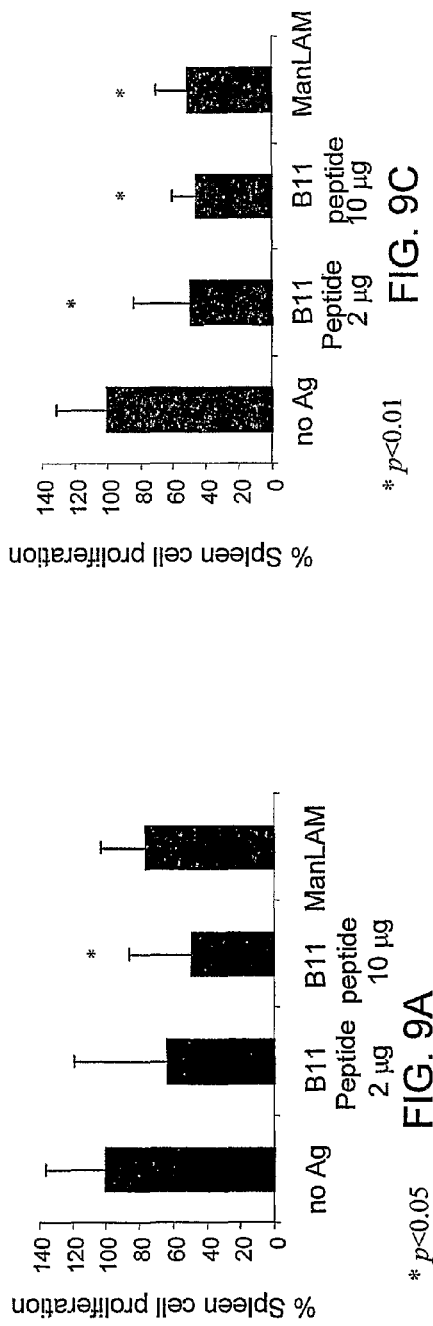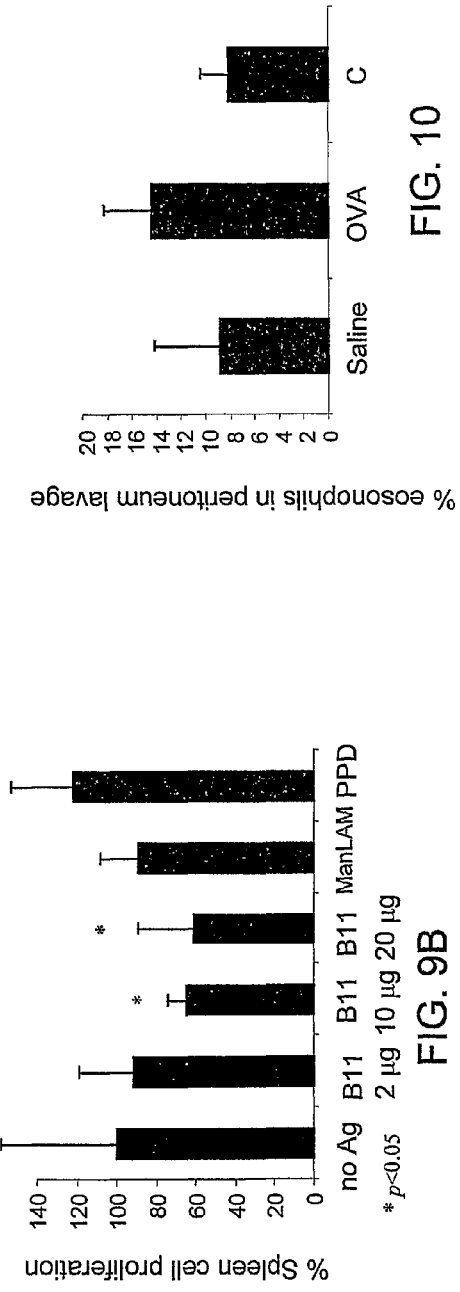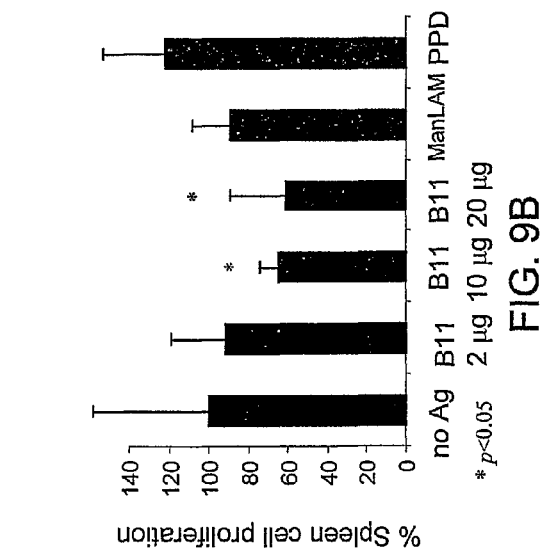

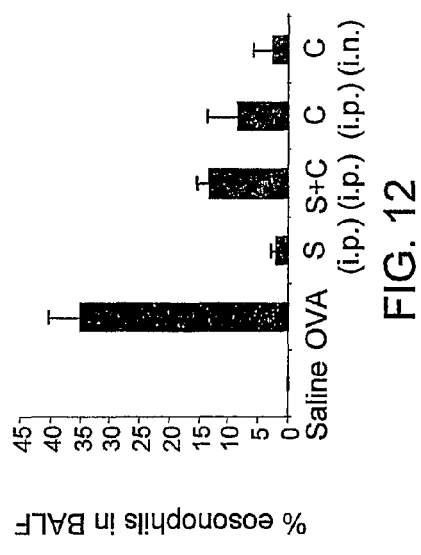
FIG. 12
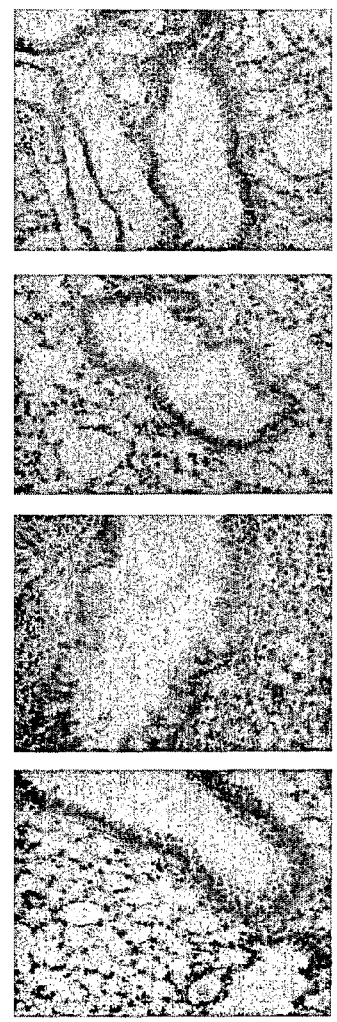
FIG. 13A
FIG. 13B
FIG. 13C
FIG. 13D

USE OF MYCOBACTERIAL MANNOSYLATED LIPOGLYCANS PEPTIDE MIMOTOPES FOR TREATING INFLAMMATION

CROSS-REFERENCE

This is a National Phase Application filed under 35 U.S.C. 371 of International Application No. PCT/IL2005/000674, filed Jun. 23, 2005, claiming the benefit under 35 USC 119(e) of U.S. Provisional Application No. 60/582,221, filed Jun. 24, 2004, the entire contents of each of which is hereby incorporated herein by reference in its entirety.

FIELD OF THE INVENTION

This invention relates in general to treatment of inflammatory conditions and specifically to the use of amino acid molecules for the treatment of these conditions.

LIST OF PRIOR ART

The following is a list of prior art considered to be relevant to the subject matter of the present invention:
Quesniaux, V., et al. *J. Immunol.* 172:4425-34 (2004);
Barnes P. et al., *J. Immunol.* 149:541-7. (1992);
Shirakawa T et al., *Science.* 275:77-9. (1997);
Mutius E. et al., *Thorax.* 55: 449-53 (2000);
Shirtcliffe P. et al., *Respirology.* 7: 153-5. (2002);
Hubeau C. et al *Clin Exp Allergy.* 33:386-93. (2003);
Chatterjee, D., et al. *J Biol Chem* 267: 6234-6239 (1992);
Prinzis, S., et al. *J Gen Microbiol* 139: 2649-2658 (1993);
WO 03/049752;
Agrawal D. et al., *Int Immunopharmacol.* 4:127-38. (2004)
Yoshimora S. et al., *Eur J Immunol.* 31:1883-93 (2001)

BACKGROUND OF THE INVENTION

*Mycobacterium* species have shown anti-inflammatory and immuno-regulatory effects in various cases [Zuany-Amorim et al., *Nature medicine.* 8: 625-629 (2002)]. In people a correlation was found between exposure to BCG or Mtb and inhibition of atopic disorders. Positive tuberculin responses predicted a lower incidence of asthma, lower serum IgE levels, and cytokine profiles biased toward $T_H1$ type. Exposure and response to *M. tuberculosis* (Mtb) may, by modification of immune profiles, inhibit atopic disorder [Shirakawa et al. (1997)]. Ecological analyses have repeatedly and consistently found an inverse association between the prevalence of tuberculosis in a given country and the prevalence of atopic disorders [von Mutius et al., (2000) ibid, Shirtcliffe et al. (2002) ibid].

The anti-inflammatory and immunoregulatory effects of mycobacteria species have also been observed in several murine models. In allergic asthma mice model induced by ovalbumin (OVA), mice showed high levels of both Th1 and Th2 cytokine transcripts, mice pre-treated with BCG showed transcript levels similar to normal controls, suggesting that the pre-immunization with BCG restores the Th1/Th2 balance [Hubeau et al., (2003)]. The use of killed mycobacterial preparation in the treatment of diseases comprising an immune dysregulation was described in WO03049752. According to this publication, compositions comprising killed mycobacteria or fractions thereof (killed in a manner by which the molecules do not denaturate) are useful for the treatment of Th1-Th2 imbalance, which may result in a variety of conditions including cancer, autoimmune diseases and allergic disorders.

*Mycobacterium* Cell Wall-associated Lipoglycans

Lipoarabinomannans (LAMs) polysaccharides are major cell surface components of *Mycobacterium* sp. as Mtb. LAMs are phosphatidylinositol-anchored lipoglycans composed of a mannan core with oligoarabinosyl-containing side-chains with diverse biological activities. These polysaccharide accounts for up to 5 mg g−1 bacterial weight. LAM structures differ according to mycobacterial species, and three general classes of LAM have been described: (i) ManLAM, from the virulent strains Erdman and H37Rv and the avirulent strains H37Ra and BCG [Chatterjee, D., et al. *J* (1992) ibid; Prinzis, S., et al. *Gen Microbiol* 139:2649-2658 (1993)], which is characterized by extensive mannose capping of the arabinan termini; (ii) phospho-myo-inositol-capped LAM (PILAM), found in the rapidly growing mycobacteria *M smegmatis* and *M. fortuitum* [Nigou, *J. Biochimie* 85:153-166 (2003)]; and (iii) phosphatidylinositol-capped LAM (AraLAM), which was described in the rapidly growing *M. chelonae* and lacks mannosylation in its arabinan termini [Guerardel, Y., et al. *J Biol Chem* 277:30635-30648 (2002)]. Although there is significant heterogeneity between LAM molecules with respect to glycosylation and acylation [Nigou et al. (2003) ibid.], differences in biological activity between the major classes of LAM have been attributed primarily to the heavy mannose capping of ManLAM [Chatterjee et al. (1992). ibid.]

LAMs have been shown to be immunomodulators that modulate cytokine responses and proliferation, in several models. Typically, ManLAM from pathogenic mycobacteria have been reported to be anti-inflammatory, whereas PILAM from nonpathogenic species are pro-inflammatory molecules [Quesniaux et al. (2004). ibid]. TNF and IL-12 release in human dendritic cell line THP-1 and in primary murine macrophages stimulated with LPS was inhibited by ManLAM from *M. bovis*, BCG and *M. tuberculosis* [Quesniaux et al. (2004). ibid]. Antigen induced proliferation of Peripheral Blood Mononuclear Cells (PBMC) was inhibited by LAM [Barnes et al. (1992). Ibid].

Inflammation and Immune Responses

Immune processes are probably ongoing and, in most cases, lead to the elimination of antigens without producing clinically detectable inflammation. The development of clinically apparent inflammation indicates that the immune system has encountered either an unusually large amount of antigen, antigen in an unusual location, or antigen that is difficult to digest or that is processed in a way that results in an inflammation or an autoimmune disease. In some diseases, such as rheumatoid arthritis, the initiating agent is unknown or may be normal host tissue components. In others (e.g. systemic lupus erythematosus), inherent or acquired immunoregulatory abnormalities may contribute to the sustained nature of the inflammatory process.

Inflammatory responses and immune induced pathologies mediated by the immune system are divided into four categories, called I, II, III, and IV, which represent four distinct immune mechanisms.

I. Immediate hypersensitivity (allergic, or reaginic acute inflammation).

II. Cytotoxic (inflammation mediated by cytotoxic antibodies).

III. Immune complex (inflammation mediated by immune complex).

IV. Delayed hypersensitivity (chronic inflammation mediated by lymphocytes and macrophages).

Each of the above mechanisms may result in the development of inflammatory conditions which require therapeutic treatment.

SUMMARY OF THE INVENTION

By screening through random phage display libraries, peptide mimotopes of Mannosylated Lipoarabinomannan (ManLAM) have been identified. As described in co-pending International Patent Application No. IL/2005/000199 and herein below, these ManLAM mimotopes are capable of specifically binding to anti-ManLAM antibodies, and of eliciting an immune response in a subject inoculated therewith, giving rise to production of ManLAM-binding antibodies.

A particular ManLAM mimotope (referred to herein as the B11 peptide) was further investigated. It has now been found that this B11 peptide has anti-inflammatory and immunomodulatory effects similar, albeit, not identical, to those induced by ManLAM in murine macrophage cell line, primary spleen cells and human monocyte cell line THP-1. Specifically, in addition to its diagnostic and immunizing effect described in the co-pending PCT IL/2005/000199 and herein below, the B11 peptide has now demonstrated anti-inflammatory effects in a number of animal models, including septic shock models of mice injected with lipopolysaccharide (LPS), allergic peritonitis murine model, allergic asthma murine model, and Crohn's disease model in mice (TNBS induced colitis).

Peptide mimotopes are compounds that mimic the structure of an epitope and provoke an antibody response to the molecule they mimic. The compounds may be of the same or of a different type of molecule as the original epitope. The term "mimotope" [Meloen R. et al. *J. Mol. Recognit.* 13:352-359 (2000)] is also known in the art by the terms "mimitope" [Arnold G. et al. *Intervirology* 39:72-78 (1996)]; "mimotype" [Benhar I. *Biotechnol. Adv.* 19:1-33 (2001)]; "mimetic" [Vyas et al. *Proc. Natl. Acad. Sci. USA* 100:15023-15028 (2003)].

Thus, according to a first aspect, the present invention provides the use of a molecule comprising a peptide having one or more of the following characteristics:
  (a) it can bind to ManLAM binding antibodies;
  (b) it can elicit an immune response in a subject inoculated therewith, giving rise to production of ManLAM-binding antibodies;
for the production of a pharmaceutical composition for the treatment of an inflammatory condition.

The invention also provides a method of treatment of an inflammatory condition in a subject in need thereof, the method comprising administering to said subject with an anti-inflammatory amount of a molecule as defined above, the amount being effective to treat an inflammatory condition in the subject.

Further, the invention provides a pharmaceutical composition for the treatment of an inflammatory condition in a subject, the composition comprising a physiologically acceptable carrier and an amount of a molecule as defined above, the amount being effective to treat an inflammatory condition in the subject.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIGS. 2A-2D are bar graphs showing ManLAM-binding antibodies produced in B11 immunized mice: IgG in phage immunized mice (FIG. 1A) IgM (FIG. 1B) IgG (FIG. 1C) and IgQ isotypes (FIG. 1D) in synthetic, KLH-peptide immunized mice.

FIGS. 5A-5C are images showing the binding of B11 FITC-labeled peptide to the macrophage RAW 264.7 cell line as is illustrated by confocal micrograph (FIG. 5A) and FACS analysis (FIG. 5B), quantifying the fluorescence levels corresponding to the binding of the B11 FITC-labeled peptide, and the reduction of binding when 0.125 M D-mannose was added (FIG. 5C)

FIGS. 9A-9C are bar graphs showing that B11 peptides inhibits the proliferation of murine spleen cells of naive (FIG. 9A), Mtb infected (FIG. 9B), and adjuvant stimulated BALB/c mice (FIG. 9C) as measured in proliferation assays.

FIG. 10 is a bar graph showing that in an OVA induced allergic peritonitis (OVA), model treatment with 200 μg B11-peptide 1 hour before challenge (C) eosonophils levels in the peritoneum lavage (PLF) are as in the saline sensitized mice (saline) and significantly different than in the mice induced with OVA as measured by FACS analysis with Phycoerytrin (PE)-labeled anti-CCR3 Ab

FIG. 12 is a bar graph showing that in an OVA induced allergic asthma model treatment of mice with 200 μg B11-peptide reduced eosonophilia in bronchoalveolar lavage (BALF) vs. the OVA sensitized and challenged group (OVA) at various times of peptide treatment: S i.p.—2 days before OVA sensitization; C i.p—two days before challenge; C i.n.—one hour before challenge; S+C—two days before both sensitization and challenge; as measured in the BALF by FACS analysis Phycoerytrin (PE)-labeled anti-CCR3Ab.

FIG. 13A-13D are photomicrographs after Hematoxylin eosin (HE) staining showing histology of murine lung sections after OVA intranasal challenge and different treatment with B11 peptide (200 µg per mouse per treatment), FIG. 13A is a negative control (non-sensitized); FIG. 13B sensitized and challenged with OVA; FIG. 13C of pretreated i.p. with B11 before sensitizations; and FIG. 13D of mice pretreated i.p. with 200 µg/mouse B11 before challenges. All the pictures were taken at the same magnification (40×10).

DESCRIPTION OF THE INVENTION

Figures 1A, 1B:
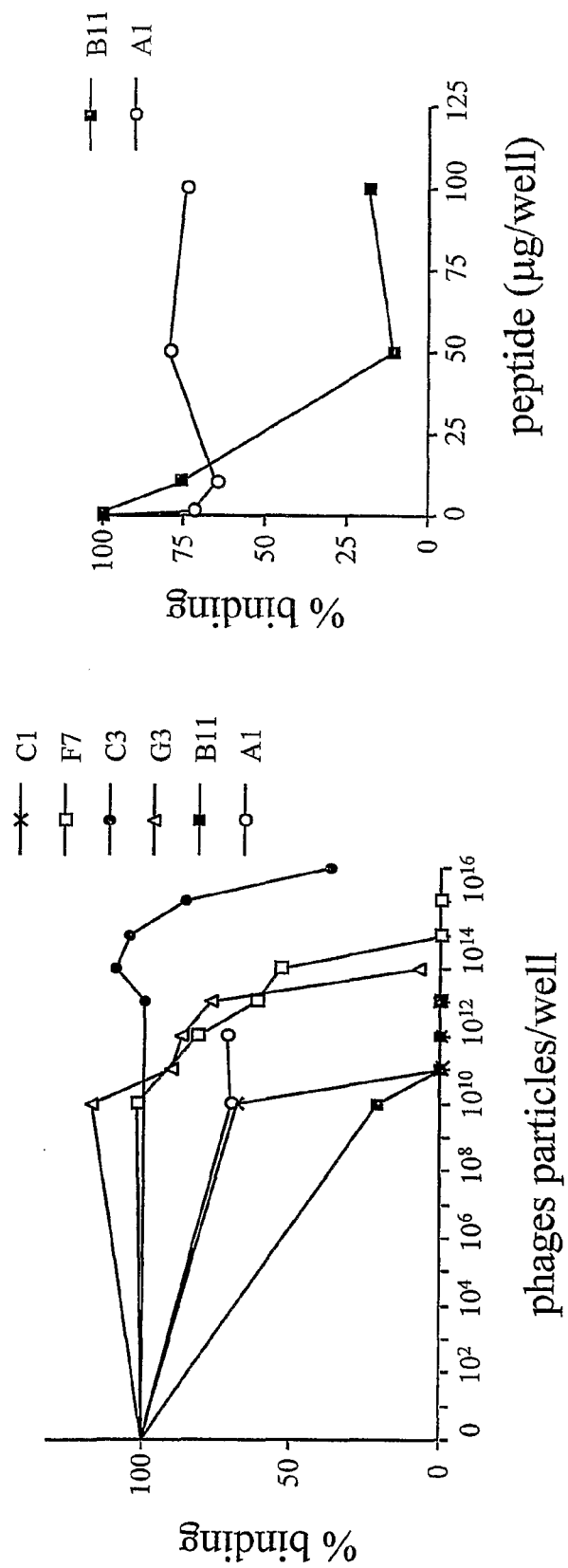
FIGS. 1A-1B are graphs showing competitive binding (% binding) vs. ManLAM of phage clones presenting different peptides (FIG. 1A) or of synthetic peptides B11 and A1 (FIG. 1B) to CS40 anti-ManLAM monoclonal antibody.

The present invention is based on the discovery that biological peptide-based mimotopes of mannose-containing cell-wall compounds of *Mycobacterium tuberculosis*, specifically, ManLAM, have an anti-inflammatory effect and immunoregulator effect in animal models of inflammation. Such models include animal models of allergic peritonitis, allergic asthma and septic shock model (mice injected with LPS) and in Crohn's disease model (TNBS-induced colitis). A specific peptide mimotope exemplified hereinbelow is the B11 peptide (SEQ ID NO:1). This peptide was shown to modify and/or inhibit secretion of cytokines in the aforementioned models.

As appreciated by those versed in the art, cytokines have an important role in the immune response. Cytokines constitute a group of low molecular weight soluble proteins that are transiently and locally released in response to various stimuli. These proteins are produced by immune cells. Cytokines mediate a variety of immunoregulatory functions of target cells, activating signal, controlling the intensity and kinetics of a particular immune response by inducing or inhibiting the activation, proliferation, and/or differentiation of various target cells, they also regulate the production of other cytokines [Salazar-Mather and Hokeness (2003)].

Changes in cytokine secretions have been shown to have effect on inflammation in several models. It was found in the murine OVA induced allergic asthma model that in treatments that reduced eosonophilia in the BALF, there was suppression of IL-4 and IL-10 [Agrawal et al., (2004) ibid]. Reducing IL-4 in BAL cells inhibits eosinophilia in BALF, indicating that IL-4 is important for the propagation of cytokine signals within the airways early following allergen challenge [Martin J. et al., *Paediatr Respir Rev.;* 5 Suppl A:S47-51. (2004)].

The murine chronic colitis model induced by intrarectal administration of trinitrobenzene sulfonic acid (TNBS) resembles many of the clinical, histopathologic, and immune characteristics of colitis in humans. This inflammation is characterized by a massive infiltration of neutrophils and macrophages, producing high levels of pro-inflammatory cytokines. In treatment that has successfully reduced the colitis a reduction in the pro-inflammatory cytokine levels was observed [Abad C. et al., *Gastroenterology.* 124:961-71. (2003)].

Generally inhibition of the immunostimulatory cytokines IL-12 and TNF-α, and INF-γ influence many factors in the immune system. This has implications for the development of therapeutic agents for use in multiple conditions, including transplantation, allergy and autoimmune diseases [Yoshimura et al., (2001)].

A connection between inflammation and apoptotic cells has also been found in a few pathologies such as rheumatic arthritis [Leech M. et al., *Arthritis Rheum.* 48:1881-9 (2003)], and colitis [D'Argenio G. Int *J Colorectal Dis.* 19:451-60. (2004); Wu W. and Cho C. *J Pharmacol Sci.* 94:348-58. (2004)].

Thus, according to a first of its aspects, the invention provides the use a molecule, particularly, an amino acid based molecule, comprising one or more peptides (which may be the same or different in sequence), the peptide having one or more of the following characteristics:
   (a) it can bind to ManLAM binding antibodies;
   (b) it can elicit an immune response in a subject inoculated therewith, giving rise to production of ManLAM-binding antibodies;
for the production of a pharmaceutical composition for the treatment of an inflammatory condition.

The term "amino acid based molecule" (hereinafter the "molecule") denotes a molecule which in addition to amino acids forming the peptide, may comprise other constituents, such as low molecular weight compounds (e.g. sugar moieties, lipid moieties), polymers (amino acid polymer, lipid polymer, polysaccharide) etc. In other words, the term "amino-acid based molecule" should be construed as encompassing also conjugates, in which, for example, the peptide is linked to other functional moieties, such as carriers, active compounds, as further detailed hereinafter.

The amino acids may comprise naturally occurring as well as non-naturally occurring amino acids.

The term "naturally occurring amino acid" refers to a moiety found within a peptide and is represented by —NH—CHR—CO—, wherein R corresponds to the side chain of the 20 naturally appearing amino acids.

The term "non-naturally occurring amino acid" (amino acid analog) is either a peptidomimetic, or is a D or L residue having the following formula: —NH—CHR—CO—, wherein R is an aliphatic group, a substituted aliphatic group, a benzyl group, a substituted benzyl group, an aromatic group or a substituted aromatic group and wherein R does not correspond to the side chain of a naturally-occurring amino acid. This term also refers to the D-amino acid counterpart of naturally occurring amino acids.

Amino acid analogs are well known in the art; a large number of these analogs are commercially available. Many times the use of non-naturally occurring amino acids in the peptide has the advantage that the amino acid molecule is more resistant to degradation by enzymes which fail to recognize them.

Further, the molecule of the invention may include amino acids which have been chemically modified.

"Chemical modification" includes modification at the side chain of the amino acid residue, as well as modification of the peptidic bond. Accordingly, a functional group may be added to the side chain, deleted from the side chain or exchanged with another functional group. Typically, the modifications are conservative modifications resulting in conservative substitution. Examples of conservative modifications of this type include adding an amine or hydroxyl, carboxylic acid to the aliphatic side chain of valine, leucine or isoleucine, exchanging the carboxylic acid in the side chain of aspartic acid or glutamic acid with an amine or deleting the amine group in the side chain of lysine or ornithine.

Other chemical modifications known in the art include arboxymethylation, acylation, phosphorylation, glycosylation or fatty acylation, and others.

The term "modification" also includes alteration of a bond within the peptidic backbone, i.e. that the bond between the N— of one amino acid residue to the C— of the next has been altered to non-naturally occurring bonds by reduction (to —CH$_2$—NH—), alkylation (methylation) on the nitrogen atom, or the bonds have been replaced by amidic bond, urea bonds, or sulfonamide bond, etheric bond (—CH$_2$—O—), thioetheric bond (—CH$_2$—S—), or to —C—S—NH—; The side chain of the residue may be shifted to the backbone nitrogen to obtain N-alkylated-Gly (a peptidoid).

Modification also includes cyclization of the amino acid molecule, e.g. by forming S—S bonds. S—S bonds may be formed via the inclusion of sulphor-containing amino acid residues, such as cysteine at each terminus of the amino acid molecule. Cyclic peptides have been shown to be more stable and with higher biological activity than the corresponding linear molecule [Jining L. et al. *Eur. J. biochem* 271:2873-2886 (2004)].

According to the invention, the modification should be such that the effect of the molecule resulting from said modification, on the immune response manifested in a subject during an inflammatory state (i.e. the anti-inflammatory effect) is substantially retained or increased as compared to the original molecule from which the modified molecule is derived. Preferably, the modification should be such that the effect of the resulting molecule correlates or is increased with respect to the anti-inflammatory effect of a molecule comprising or consisting of the peptide having the sequence ISLTEWSMWYRH (SEQ ID NO:1) named herein as the B11 peptide.

The molecules of the invention may also be modified by substitutions, insertions/additions or deletions of one or more amino acid residue in a peptide having the above-defined characteristics as long as the anti-inflammatory effect of the resulting (modified) molecule is essentially the same or is increases with respect to the molecule from the resulting molecule is derived.

The term "substitution" includes the replacement of one or more amino acid residues either by other naturally occurring amino acids, (conservative and non-conservative substitutions), by non-naturally occurring amino acids (conservative and non-conservative substitutions), or with organic moieties which serve either as true peptidomimetics (i.e., having the same steric and electrochemical properties as the replaced amino acid), or merely serve as spacers in lieu of an amino acid, so as to keep the spatial relations between the amino acid spanning this replaced amino acid.

The term "conservative substitution" in the context of the present invention refers to the replacement of an original amino acid present in the identified amino acid molecules with a naturally or non-naturally occurring amino or a peptidomimetic residue having similar steric properties. Where the side-chain of the original amino acid to be replaced is either polar or hydrophobic, the conservative substitution should be with a naturally occurring amino acid, a non-naturally occurring amino acid or with a peptidomimetic moiety which is also polar or hydrophobic (in addition to having the same steric properties as the side-chain of the replaced amino acid). However where the original amino acid to be replaced is charged, the conservative substitution according to the definition of the invention may be with a naturally occurring amino acid, a non-naturally occurring amino acid or a peptidomimetic moiety which are charged, or with non-charged (polar, hydrophobic) amino acids that have the same steric properties as the side-chains of the replaced amino acids. The purpose of such a procedure of maintaining the steric properties but decreasing the charge is to decrease the total charge of the compound, for example for improving its membrane penetrating properties.

For example in accordance with the invention the following substitutions are considered as conservative: replacement of arginine by cytokine; arginine by glutamine; aspartate by asparagine; glutamate by glutamine.

As the naturally occurring amino acids are grouped according to their properties, conservative substitutions by naturally occurring amino acids can be easily determined bearing in mind the fact that in accordance with the invention replacement of charged amino acids by sterically similar non-charged amino acids are considered as conservative substitutions.

For producing conservative substitutions by non-naturally occurring amino acids it is also possible to use amino acid analogs (synthetic amino acids) well known in the art. A peptidomimetic of the naturally occurring amino acid is well documented in the literature known to the skilled practitioner.

The following are some non-limiting examples of groups of naturally occurring amino acids or of amino acid analogs are listed bellow. Replacement of one member in the group by another member of the group will be considered herein as conservative substitutions:

Group I includes leucine, isoleucine, valine, methionine, phenylalanine, serine, cysteine, threonine and modified amino acids having the following side chains: ethyl, n-butyl, —CH$_2$CH$_2$OH, —CH$_2$CH$_2$CH$_2$OH, —CH$_2$CHOHCH$_3$ and —CH$_2$SCH$_3$. Preferably Group I includes leucine, isoleucine, valine and methionine.

Group II includes glycine, alanine, valine, serine, cysteine, threonine and a modified amino acid having an ethyl side chain. Preferably Group II includes glycine and alanine.

Group III includes phenylalanine, phenylglycine, tyrosine, tryptophan, cyclohexylmethyl, and modified amino residues having substituted benzyl or phenyl side chains. Preferred substituents include one or more of the following: halogen, methyl, ethyl, nitro, methoxy, ethoxy and —CN. Preferably, Group III includes phenylalanine, tyrosine and tryptophan.

Group IV includes glutamic acid, aspartic acid, a substituted or unsubstituted aliphatic, aromatic or benzylic ester of glutamic or aspartic acid (e.g., methyl, ethyl, n-propyl iso-propyl, cyclohexyl, benzyl or substituted benzyl), glutamine, asparagine, CO—NH-alkylated glutamine or asparagine (e.g., methyl, ethyl, n-propyl and iso-propyl) and modified amino acids having the side chain —(CH$_2$)$_3$COOH, an ester thereof (substituted or unsubstituted aliphatic, aromatic or benzylic ester), an amide thereof and a substituted or unsubstituted N-alkylated amide thereof. Preferably, Group IV includes glutamic acid, aspartic acid, glutamine, asparagine, methyl aspartate, ethyl aspartate, benzyl aspartate and methyl glutamate, ethyl glutamate and benzyl glutamate.

Group V includes histidine, lysine, arginine, N-nitroarginine, α-cycloarginine, μ-hydroxyarginine, N-amidinocitruline and 2-amino-4-guanidinobutanoic acid, homologs of lysine, homologs of arginine and ornithine. Preferably, Group V includes histidine, lysine, arginine, and ornithine. A homolog of an amino acid includes from 1 to about 3 additional methylene units in the side chain.

Group VI includes serine, threonine, cysteine and modified amino acids having $C_1$-$C_5$ straight or branched alkyl side chains substituted with —OH or —SH. Preferably, Group VI includes serine, cysteine or threonine.

The term "non-conservative substitutions" concerns replacement of one or more amino acid residues present in the original molecule by another naturally or non-naturally occurring amino acid, having different a different size, configuration and/or electronic properties compared with the amino acid being substituted. Thus, the side chain of the substituting amino acid can be significantly larger (or smaller) than the side chain of the original amino acid being substituted and/or can have functional groups with significantly different electronic properties than the amino acid being substituted.

The amino-acid based molecule may also include peptidomimetic organic moieties. Peptidomimetics are often used to inhibit degradation of the amino acid molecules by enzymatic or other degradative processes. The peptidomimetics can be produced by organic synthetic techniques. Examples of suitable peptidomimetics include D amino acids of the corresponding L amino acids, tetrazol (Zabrocki et al., *J. Am. Chem. Soc.* 110:5875-5880 (1988)); isosteres of amide bonds (Jones et al., Tetrahedron Lett. 29: 3853-3856 (1988)); LL-3-amino-2-propenidone-6-carboxylic acid (LL-Acp) (Kemp et al., *J. Org. Chem.* 50:5834-5838 (1985)). Similar analogs are shown in Kemp et al., Tetrahedron Lett. 29:5081-5082 (1988) as well as Kemp et al., Tetrahedron Lett. 29:5057-5060 (1988), Kemp et al., Tetrahedron Lett. 29:4935-4938 (1988) and Kemp et al., *J. Org. Chem.* 54:109-115 (1987). Other suitable peptidomimetics are shown in Nagai and Sato, Tetrahedron Lett. 26:647-650 (1985); Di Maio et al., *J. Chem. Soc. Perkin Trans.*, 1687 (1985); Kahn et al., Tetrahedron Lett. 30:2317 (1989); Olson et al., *J. Am. Chem. Soc.* 112: 323-333 (1990); Garvey et al., *J. Org. Chem.* 56:436 (1990). Further suitable peptidomimetics include hydroxy-1,2,3,4-tetrahydroisoquinoline-3-carboxylate (Miyake et al., *J. Takeda Res. Labs* 43:53-76 (1989)); 1,2,3,4-tetrahydro-iso-quinoline-3-carboxylate (Kazmierski et al., *J. Am. Chem. Soc.* 133:2275-2283 (1991)); histidine isoquinolone carboxylic acid (HIC) (Zechel et al., *Int. J. Pep. Protein Res.* 43 (1991)); (2S,3S)-methyl-phenylalanine, (2S,3R)-methyl-phenylalanine, (2R,3S)-methyl-phenylalanine and (2R,3R)-methyl-phenylalanine (Kazmierski and Hruby, Tetrahedron Lett. (1991)).

"Deletion" includes exclusion of one or more amino acid residues (naturally occurring, non-naturally occurring, or peptidomimetic organic moiety) as compared to the original molecule from which it is derived.

"Insertion" or "addition" includes the addition of one or more amino acid residues (naturally occurring, non-naturally occurring, or peptidomimetic organic moiety) as compared to the original molecule from which it is derived.

Notwithstanding the above, it should be understood that the amino acid-based molecule used in accordance with the invention is not a lipoglycan and specifically is not ManLAM.

The molecules comprising one or more of the peptides characterized above and which are to be used in accordance with the present invention bind with specificity to anti-ManLAM antibodies. According to a preferred embodiment, the molecule to be used in accordance with the invention comprises a peptide characterized by its binding to ManLAM monoclonal antibodies (mAbs) and sera Abs. Specific examples of binding a mAb is the CS40 mAb (Drs. Brennan and Belisle, Colorado State University, Fort Collins, Colo., National Institute of Health grant AI-75320), binding to Abs in sera of tuberculosis (TB) patients, and to sera Abs of Mtb experimentally infected mice.

Another characteristic of the peptide to be used (as is or as part of a molecule) in accordance with the invention is that it does not bind to antibodies directed against lipoglycans selected from non-mannolsylated and low mannosylated lipoglycans. Specifically, it has been shown that the peptides having the above characteristics do not bind to CS35 anti-LAM mAb (Drs. Brennan and Belisle, Colorado State University, Fort Collins, Colo., National Institute of Health grant AI-75320), 735 anti-ploy $\alpha(2\rightarrow8)$ N-acetyl neuraminic acid mAb (Kibbelaar R. et al., *J. Pathol.* 159:23-8 (1989)), and 2H1 anti-glucuronoxylomannan mAb [Valdon P. and Scharff M. *J Immunol Methods.* 197:171-9 (1996)].

The discovery of specific peptides which fulfill one or more of the above characteristics led to the understanding that the peptide has preferentially an internal aromatic amino acid residue. Examples of naturally occurring amino acid which comply with this requirement are phenylalanine (F), histidine (H), tryptophan (W), tyrosine (Y). Without being limited to these examples, the peptides may also contain internal aromatic residues which are conservative substitutions of the above. The term "internal" as used herein signifies that the peptide consists of at least three amino acid residues, with at least one amino acid at each side of the "internal" residue. According to a preferred embodiment, the internal aromatic residue is tryptophan (W).

Another feature which may be considered as a characteristic element of the peptide to be used in accordance with the invention is the presence of a hydrophilic amino acid residue adjacent and preceding said aromatic residue.

Specific, non-limiting examples of peptides which comply with one or more of the above characteristics are:

| | |
|---|---|
| ISLTEWSMWYRH | (SEQ ID NO: 1) |
| EEGPWSTHVGRT | (SEQ ID NO: 2) |
| WGNEGGDHLQPV | (SEQ ID NO: 3) |
| SLKIRWELKMYQE | (SEQ ID NO: 4) |
| AVERWEKHTWSE | (SEQ ID NO: 5) |

Thus, the invention provides the use of a molecule comprising or consisting one or more of the above peptides and modifications thereof.

The term "modifications" includes any one of the above defined modifications as known in peptide-based technologies, all of which result in a molecule which retains the physiological character of the original molecule from which it is derived.

The term "physiological character" concerns the essential characteristics of the peptide to be used in accordance with the invention and includes: the antigenic character (i.e. the capacity to bind ManLAM binding antibodies), the immunogenic character (i.e. the capacity to elicit, upon immunization, production of ManLAM binding antibodies) of the original amino acid molecule; the anti-inflammatory character, and the inflammation condition treating character of the molecule.

A preferred embodiment of the invention provides the use of a molecule which comprises or consists of the B11 peptide, having the sequence as depicted in SEQ ID NO:1 modifications thereof for the treatment of inflammatory conditions.

Thus, in accordance with another preferred embodiment, the immunologic character of the peptide within the molecule should be such the antibody binding capacity thereof correlates with that of peptide B11, i.e. it preferentially binds to antibodies to which the peptide B11 binds and has a relatively low binding affinity to antibodies to which the peptide B11 has a low binding affinity.

The above defined molecules and peptides are used for the preparation of a pharmaceutical composition for the treatment of an inflammatory condition.

The terms "treat", "treating" and "treatment" refer to the administering of a therapeutically effective anti-inflammatory amount of the molecule or a pharmaceutical composition comprising same which is effective to ameliorate undesired symptoms associated with inflammation, to prevent the manifestation of such symptoms before they occur, to slow down the progression of an inflammatory condition, to slow down the deterioration of symptoms associated with an inflammatory condition, to slow down the irreversible damage caused by the chronic stage of an inflammatory condition, to lessen the severity or cure an inflammatory condition, to improve survival rate or more rapid recovery form such a condition.

It should be noted that in the context of the present invention the term "treatment" also denotes "prophylactic treatment", i.e. for prevention of the development of an inflammatory condition or to prevent the re-occurrence of an acute inflammatory phase in a chronically ill individual. To this end, the molecule may be administered to individuals who do not have inflammation and especially, to individuals having a high-risk of developing an inflammatory condition, e.g. as a result of injury, exposure to an infecting agent or allergen. In this case, the molecule will typically be administered over an extended period of time in a single daily dose (e.g. to produce a cumulative effective amount), in several doses a day, as a single dose for several days, etc. so as to prevent the manifestation of inflammation.

The "anti-inflammatory effective amount" for purposes herein is determined by such considerations as may be known in the art. The amount must be effective to achieve the desired anti-inflammatory effect in a subject suffering from an inflammatory state, the desired anti-inflammatory effect include, for example, amelioration of undesired symptoms associated with inflammation, prevention of the manifestation of such symptoms before they occur, slowing down progression of an inflammatory condition, slowing down the deterioration of symptoms associated with an inflammatory condition, slowing down any irreversible damage caused by a chronic stage of an inflammatory condition, lessening of the severity or curing an inflammatory condition, improving survival rate or providing more rapid recovery form such a condition. Further, in the context of prophylactic treatment the amount may also be effective to prevent the development of an inflammatory condition.

The effective amount depends, inter alia, on the type and severity of the disease to be treated and the treatment regime. The effective amount is typically determined in appropriately designed clinical trials (dose range studies) and the person versed in the art will know how to properly conduct such trials in order to determine the effective amount. As generally known, an effective amount depends on a variety of factors including the affinity of the molecule to the corresponding receptor, its distribution profile within the body, a variety of pharmacological parameters such as half life in the body, on undesired side effects, if any, on factors such as age and gender, etc.

The effective amount may be that provided in a single dose or a cumulative amount provided to a subject in several doses provided to a subject over an extended period of time (e.g. in a single daily dose) or in several doses a day.

The terms "inflammatory condition" of "inflammatory state" includes any state of active or sub-clinical inflammation, including immune induced pathologies (e.g. autoimmune disorders). The inflammation may be due to an inflammatory disease, or it may be a side effect of some other type of disease or disorder.

Inflammatory states and other immune induced pathologies which are mediated by the immune system may be divided into four categories:

I. Immediate hypersensitivity (allergic, or reaginic acute inflammation): includes type I hypersensitivity and is characterized by an allergic reaction that occurs immediately following contact with antigen (allergen). In some individuals certain allergens have a propensity to stimulate production of IgE antibodies. IgE antibodies bind nonspecifically, via their high affinity Fc receptors, to mast cells and basophils. Subsequent attachment of antigen to the Fab portion of cell-bound IgE antibodies results in release of contents of cytoplasmic granules from mast cells and basophils (e.g. histamine), as well as in synthesis and secretion of biologically active products of arachidonic acid (e.g. leukotrienes).

Allergic reactions include, without being limited thereto urticaria, seasonal rhinitis, asthma, and in settings where large amounts of antigens (allergens) enter the host circulation, systemic anaphylaxis.

Another non-limiting example of a type 1 hypersensitivity is septic shock.

II. Cytotoxic (inflammation mediated by cytotoxic antibodies): refers to Type II, or antibody-dependent cytotoxic hypersensitivity and occurs when antibody binds to either self antigen or foreign antigen on cells, and leads to phagocytosis, killer cell activity or complement-mediated lysis.

In type II hypersensitivity, also known by the term antibody directed against cell surface or tissue antigens forms immune complex which interacts with complement and a variety of effector cells to bring about damage to the target cells. Antibodies link the target cells to effectors cells, such as macrophages, neutrophils, eosinophils and generally, K cells, by means of Fc receptors on these effector cells.

Both the complement fragments and IgG can act as opsonins bound to host tissues or to microorganisms, and phagocytes take up the opsonized particles.

There are three main subtypes of cytotoxic hypersensitivity:

(a) Type II reactions between members of the same species caused by isoimmunization and include transfusion reactions after transfusion of blood incompatible in the ABO system, haemolytic disease of the newborn due to rhesus incompatibility and/or transplantation reaction provoked by antibodies in the recipient directed against surface transplantation antigens on the graft.

(b) Autoimmune type II hypersensitivity reactions evoked by antibodies in the host directed against his own cell or tissue antigens (autoantibodies). As an example may serve autoimmune haemolytic anaemia caused by autoantibodies to the patient's own red cells; Hashimoto's thyroiditis with autoantibodies against thyroid peroxidase surface antigen; idiopathic thrombocytopenic purpura manifest by platelet destruction evoked by anti-platelet antibodies; Goodpasture's syndrome in which complement-mediated damage to basement membrane due to specific autoantibodies is observed.

The following is a non-limiting list of autoimmune diseases which may be treated in accordance with the present invention: Myasthenia Gravis (MG), Congenital myasthenia gravis, Multiple sclerosis (MS), Stiff-man syndrome, Tropical spastic paraparesis, Rasmussen's encephalitis, Acute motor axonal neuropathy, Acute sensory-motor axonal neuropathy, Dorsal root ganglion neuritis, Acute pan-autonomic neuropathy, Brachial neuritis, Acute necrotizing hemorrhagic leukoencephalitis, Sporadic necrotizing myelopathy, Paraneoplastic cerebellar degeneration, Guillain-Barre syndrome, Limbic encephalitis, Opsoclonus-myoclonus ataxia, Sensory neuronitis, Autonomic neuropathy, Demyelinating neuropathy, AIDS-dementia complex, Tourette's syndrome, Miller-Fisher syndrome, Alzheimer's disease, Graves' Disease, Hashimoto's thyroiditis, Postpartum thyroiditis, Focal thyroiditis, Juvenile thyroiditis, Idiopathic hypothyroidism, Type I (insulin dependent) diabetes mellitus, Addison's disease, Hypophysitis, Autoimmune diabetes insipidus, Hypoparathyroidism, Pemphigus Vulgaris, Pemphigus Foliaceus, Bullous phemphigoid/Pemphigoid gestationis, Cicatrical pemphigoid, Dermatitis herpetiformis, Epidermal bullosa acquisita, Erythema multiforme, Herpes gestatonis, Vitiligo, Chronic urticaria, Discoid lupus, Alopecia universalis/Areata, Psoriasis, Autoimmune hepatitis, Primary biliary cirrhosis, Chronic active hepatitis, Chronic active hepatitis/Primary biliary cirrhosis overlap syndrome, Primary sclerosing cholangitis, Autoimmune hemolytic anemia, Idiopathic thrombocytopenic purpura, Evans syndrome, Heparin-induced thrombocytopenia, Primary autoimmune neutropenia, Autoimmune (primary) neutropenia of infancy, Autoimmune neutropenia following bone marrow transplant, Acquired autoimmune hemophilia, Autoimmune gastritis and pernicious anemia, Coeliac disease, Crohn's disease, Ulcerative colitis, inflammatory bowel diseases (IBD), Sialadenitis, Autoimmune premature ovarian failure, Azoospermia, Hypogonadism, Male infertility associated with sperm autoantibodies, Autoimmune orchitis, Premature ovarian failure, Autoimmune oophoritis, Uveitis, Retinitis, Sympathetic ophthalmia, Birdshot retinochoroidopathy, Vogt-Koyanagi-Harada granulomatous uveitis, Retinal degeneration, Lens-induced uveitis, Optic neuritis, Autoimmune sensorineural hearing loss, Meniere's disease, Autoimmune myocarditis, Congenital heart block (neonatal lupus), Chagas' disease, Adriamycin cardiotoxicity, Dressler's myocarditis syndrome, Bronchial asthma, Interstitial fibrosing lung disease, Rapidly progressive glomerulonephritis, Autoimmune tubulointerstitial nephritis, Systemic lupus erythematosus (SLE), Antiphospholipid syndrome, Rheumatoid arthritis, Juvenile Rheumatoid arthritis, Felty's syndrome, Large granular lymphocytosis (LGL), Sjogren's syndrome, Systemic sclerosis (scleroderma), Crest syndrome, Mixed connective tissue disease, Polymyositis/dermatomyositis, Goodpasture's Disease, Wegener's granulomatosis, Churg-Strauss syndrome, Henoch-Schonlein purpura, Microscopic polyangiatis, Periarteritis nodosa, Bechet's syndrome, Atherosclerosis, Temporal (giant) cell arteritis, Takayasu arteritis, Kawasaki disease, Ankylosing spondilitis, Reiter's disease, Sneddons disease, Autoimmune polyendocrinopathy, candidiasis-ectodermal dystropy, Essential cryoglobulinemic vasculitis, Cutaneous leukocytoclastic angiitis, Lyme disease, Rheumatic fever and heart disease, Eosinophilic fasciitis, Paroxysmal cold hemoglobinuria, Polymyalgia rheumatica, Fibromyalgia, POEMS syndrome (polyneuropathy, organomegaly, endocrinopathy, M-spot and skin changes), Relapsing polychondritis, Autoimmune lymphoproliferative syndrome, TINU syndrome (acute tubulointerstitial nephritis and uveitis), Common variable immunodeficiency, TAP (transporter associated with antigen presentation) deficiency, Omenn syndrome, HyperIgM syndrome, BTK agammaglobulinemia, Human immunodeficiency virus and Post bone-marrow-transplant.

(c) Type II drug reactions in which drugs may become coupled to body components and thereby undergo conversion from a hapten to a full antigen which may sensitive certain individuals. If, during this response, IgE antibodies are produced, anaphylactic reactions can result. In some circumstances, cell-mediated hypersensitivity may by induced. In other cases where coupling to serum proteins occurs, the possibility of type III immune complex-mediated reactions may arise. Finally, the drug antigenic complex with a molecule on the surface of host cells may evoke the production of antibodies which are cytotoxic for the cell-drug complex. Examples of this mechanism have been seen in the haemolytic anaemia sometimes associated with continued administration of chlorpromazine or phenacetin, in the agranulocytosis associated with the taking of amidopyrine or of quinidine, and classic situation of thrombocytopenic purpura which may be produced by a sedative edormid. When the drug is withdrawn, the hypersensitivity is no longer evident.

III. Immune complex (inflammation mediated by immune complex) which may be broadly divided into three groups:

(a) A combined effect of a low-grade persistent infection together with a weak antibody response, leading to chronic immune complex formation with the eventual deposition of complexes in the tissues.

(b) Immune complex disease as a complication of autoimmune disease where the continued produced of antibody to a self-antigen leads to prolonged immune complex formation. The mononuclear phagocyte, erythrocyte, and complement systems (which are responsible for the removal of complexes) become overloaded and the complexes are deposited in the tissues, as occurs in systemic lupus erythematosus.

(c) Immune complexes formed at body surfaces, notably in the lungs following repeated inhalation of antigenic material from moulds, plants or animals. This is exemplified in Farmer's lung and Pigeon fancier's lung, where there are circulating antibodies to the actinomycete fungi found in mouldy hay, or to pigeon antigens. Both diseases are forms of extrinsic allergic alveolitis, and they only occur after repeated exposure to the antigen.

IV. Delayed hypersensitivity (chronic inflammation mediated by lymphocytes and macrophages, DTH)—manifested when antigens (for example those of tubercle bacilli) are trapped in a macrophage and cannot be cleared. T cells are then stimulated to elaborate lymphokines which mediate a range of inflammatory responses. Other aspects of DTH reactions are seen in graft rejection and allergic contact dermatitis. DTH is used as a general category to describe all those hypersensitivity reactions which take more than 12 hours to develop, and which involve cell-mediated immune reactions rather than humoral immune reactions. Whereas allergic reactions occur within seconds and minutes and immune complex reactions occur within several hours to one day, DTH reactions peak at 2 to 3 days.

Three types of delayed hypersensitivity reaction are recognized: Contact hypersensitivity and tuberculin-type hypersensitivity both occur within 72 hours of antigen challenge, whereas granulomatous reactions develop over a period of weeks. The granulomas are formed by the aggregation and proliferation of macrophages, and may persist for week.

Thus, as stated above, the present invention concerns the use of the amino-acid based molecule for the preparation of a pharmaceutical composition for the treatment (including prophylactic treatment) of any of the above defined inflammatory conditions.

According to one preferred embodiment, the inflammatory condition is associated with an allergic reaction selected from asthma, allergic rhinitis and atopic dermatitis.

According to another preferred embodiment, the inflammatory condition is associated with an autoimmune response selected from multiple sclerosis, rheumatoid arthritis, Crohn's disease & colitis (collectively referred to as IBD-Inflammatory Bowel disease) and diabetes mellitus.

The invention also provides a method of treatment of an inflammatory condition in a subject in need thereof, the method comprising providing said subject with an anti-inflammatory effective amount of a molecule as defined herein.

Further, the invention provides a pharmaceutical composition for the treatment of an inflammatory condition in a subject, the composition comprising a physiologically acceptable carrier and an anti-inflammatory effective amount of the molecule as defined herein.

The "phyisiologically acceptable carrier" refers to any substance combined with the amino-acid molecule as defined and includes, without being limited thereto, diluents, excipients, carriers, solid or liquid fillers or encapsulating materials which are typically added to formulations to give them a form or consistency when it is given in a specific form, e.g. in pill form, as a simple syrup, aromatic powder, and other various elixirs. The carrier may also be substances for providing the formulation with stability, sterility and isotonicity (e.g. antimicrobial preservatives, antioxidants, chelating agents and buffers), for preventing the action of microorganisms (e.g. antimicrobial and antifungal agents, such as parabens, chlorobutanol, phenol, sorbic acid and the like) or for providing the formulation with an edible flavor etc.

The carrier can be any of those conventionally used in pharmacy and are limited only by chemico-physical considerations, such as solubility, lack of reactivity with the amino acid molecule, or by the route of administration.

According to one embodiment, the carrier is an agent which facilitates the delivery of the amino acid molecule to a target cell or tissue. As appreciated by those versed in the art, the development of peptide drugs and therapeutic proteins is limited by the poor permeability and the selectivity of the cell membrane. There is a growing effort to circumvent these problems by designing strategies to deliver full-length proteins into a large number of cells.

A specific example of a carrier which facilitates delivery of drugs, including peptides and proteins, include lipids assembly. Lipid assemblies include an organized collection of lipid or lipid like molecules forming inter alia, micelles and liposomes. The amino acid molecule-lipid assemblies includes loading, encapsulation, containment, or any other physical attachment/association between amino acid molecule and the lipid assembly. The physical attachment may be either containment or entrapment of the molecule within assemblies e.g. when vesicles are formed; non-covalent linkage of the amino acid molecule to the surface such assemblies, or embedment of the amino acid molecule in between lipid layer forming such assemblies (vesicles, micelles or other assemblies). The interaction may also include adsorption to the surface of the assembly.

The carrier may also include microspheres produced using naturally occurring or synthetic polymers. Examples of microspheres commonly used for oral delivery of (e.g. by inhalation) are the synthetic polymers, polylactic acid (PLA) and polylactic-co-glycolic acid (PLGA), sodium hyaluronate, calcium phosphate-polyethylene glycol (PEG) particles and oligosaccharide derivatives. Other options include natural polymers such as albumin, gelatin, chitosan, and dextran.

Further, a series of small protein domains, termed protein transduction domains (PTDs), have been shown to cross biological membranes efficiently and independently of transporters or specific receptors, and to promote the delivery of peptides and proteins into cells. TAT protein from human immunodeficiency virus (HIV-1), is one example of such PTDs, and was shown to effectively deliver biologically active proteins in vivo. Thus, PTDs based carriers may also be used in the context of the present invention.

It should be appreciated that the peptide in accordance with the invention may be used as is, as part of the amino acid based molecule or as an entity conjugated to another functional moiety. The functional moiety may be, for example, a polymeric carrier, e.g. polyethylene glycol to form PEGylated peptide/protein, or, alternatively, the peptide may be conjugated to a therapeutically active moiety, e.g. another peptide or a low molecular weight compound having a therapeutic effect. For example, the peptide may be conjugated with a steroid, a non-steroidal anti inflammatory drug (NSAID) or the like. Thus, the term "amino acid based molecule" used herein also encompasses such conjugates.

The pharmaceutical compositions of the invention may be presented and administered in a unit dosage form and may be prepared by any of the methods known in the art of pharmacy. All methods include the step of bringing the peptide containing molecule as defined herein in association with a carrier which may constitutes one or more ingredients. In general, the compositions are prepared by uniformly and intimately bringing the amino acid molecule in association with, for example, a liquid carrier, a waxy solid carrier or a finely divided solid carrier, and then, if needed, shaping the product into desired dosage form.

The compositions of the invention are preferably in any form suitable for systemic delivery of the amino acid molecule defined herein, such as, without being limited thereto, oral, parenteral (including subcutaneous, intramuscular and intravenous, intraarterial, intraperitoneally and intranasal), rectal or intravaginal administration as well as by infusion techniques.

According to one preferred embodiment, the composition is formulated in a form suitable for oral administration. Composition suitable for oral administration may be presented as discrete units such as capsules, cachets, tablets or lozenges, each containing a predetermined amount of aspartic acid; as a powder or granules; or a suspension or solution in an aqueous liquid or non-aqueous liquid, e.g., a syrup, an elixir, or an emulsion.

A tablet may be made by compression or molding, optionally with one or more accessory ingredients. Compressed tablets may be prepared by compressing in a suitable machine the amino acid molecule in a free flowing form, e.g., a powder or granules, optionally mixed with accessory ingredients, e.g., binders, lubricants, inert diluents, disintegrating agents or coloring agents. Molded tablets may be made by molding in a suitable machine a mixture of the amino acid molecule, preferably in powdered form, with a suitable carrier. Suitable binders include, without limitation, starch, gelatin, natural sugars such as glucose or beta-lactose, corn sweeteners, natural and synthetic gums such as acacia, tragacanth or sodium alginate, carboxymethyl-cellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

Oral liquid forms, such as syrups or suspensions in suitably flavored suspending or dispersing agents such as the synthetic and natural gums, for example, tragacanth, acacia, methyl cellulose and the like may be made by adding aspartic acid to the solution or suspension. Additional dispersing agents which may be employed include glycerin and the like.

Compositions suitable for parenteral administration include sterile aqueous preparations of the amino acid molecule which are preferably isotonic with the blood of the sub.

Such compositions suitably comprise a solution or suspension of the amino acid molecule that is isotonic with the blood of the recipient subject.

According to one preferred embodiment, the compositions of the invention are in a form suitable for injection. The requirements for effective pharmaceutical carriers for injectable compositions are well known to those of ordinary skill in the art. See *Pharmaceutics and Pharmacy Practice*, J.B. Lippincott Co., Philadelphia, Pa., Banker and Chalmers, eds., pages 238-250 (1982), and *ASHP Handbook on Injectable Drugs*, Toissel, 4$^{th}$ ed., pages 622-630 (1986).

Compositions suitable for rectal administration may be presented as a suppository with a conventional carrier, i.e., a base that is nontoxic and nonirritating to mucous membranes, compatible with amino acid molecules, and is stable in storage and does not bind or interfere with the release of the amino acid molecule. Suitable bases include: cocoa butter (theobroma oil), polyethylene glycols (such as carbowax and polyglycols), glycol-surfactant combinations, polyoxyl 40 stearate, polyoxyethylene sorbitan fatty acid esters (such as Tween, Myrj, and Arlacel), glycerinated gelatin, and hydrogenated vegetable oils. When glycerinated gelatin suppositories are used, a preservative such as methylparaben or propylparaben may be employed.

Finally, compositions suitable for intravaginal administration may be presented as pessaries, tampons, creams, gels, pastes, foams, or spray formulas containing, in addition to the amino acid molecule, such carriers as are known in the art to be appropriate.

It is noted that humans are treated generally longer than experimental animals, which treatment has a length proportional to the length of the disease process and active agent effectiveness. The amino acid molecule and compositions comprising the same as set forth hereinabove and below are administered and dosed in accordance with good medical practice, taking into account the clinical conditions of the individual patient, the site and method of administration, scheduling of administration, individual's age, sex, body weight and other factors known to medical practitioners.

The dose may be single doses or multiple doses over a period of several days. The treatment generally has a length proportional to the length of the disease process and drug effectiveness and the individual species being treated. Suitable doses and dosage regimens can be determined by conventional range-finding techniques known to those of ordinary skill in the art. Generally, treatment is initiated with smaller dosages, which are less than the optimum dose of the compound. Thereafter, the dosage is increased by small increments, until the optimum effect under the circumstances is reached.

The invention has been described in an illustrative manner, and it is to be understood that the terminology which has been used, is intended to be in the nature of words of description rather than of limitation. Obviously, many modifications and variations of the present invention are possible in light of the above teaching. It is therefore, to be understood that within the scope of the appended claims, the invention may be practiced otherwise than as specifically described hereinafter.

DESCRIPTION OF EXEMPLARY EMBODIMENTS

Materials and Methods

Biopanning of Phage Display Libraries

Phage display libraries were constructed in the fth1 type 88 vector [Enshell-Seijffers D, and Gershoni, J. M. epitopes, In *Current Protocols in Immunology*, Vol. 2. J. E. Coligan. ed. Wiley, New York. p. 9.8.1 (2002)]; Stern, B., et al. Faseb J 11, 147-153 (1997)] at the laboratory of Prof. Gershoni (Department of Cell Research and Immunology, George S. Wise Faculty of Life Sciences, Tel Aviv University, Israel).

Biopanning of random phage display libraries was performed as described in Enshell-Seijffers and Gershoni [Enshell-Seijffers and Gershoni (2002), ibid.], based on the methods of Smith and Scott, [Smith, G. P., and Scott, J. K. *Methods Enzymol* 217:228-257 (1993)]. Briefly, 6-well polystyrene plates (Nunc, Roskilde, Denmark) were coated with mAbs (5 µg/well) in TBS and then blocked with TBS/0.25% gelatin for 2 h at RT. Phage particles ($1 \times 10^{11}$) in TBS/0.25% gelatin were bound to the mAb-coated wells at 4° C. for 16 h. The unbound phages were removed by 4 washes of TBS, and the bound phages were eluted by adding a glycine/HCl/BSA buffer, pH 2.2, for 10 min, which was then neutralized using Tris buffer, pH 9.1. Phages were amplified in *Escherichia coli* DH5a. For titer determination, aliquots of the eluate or the amplificate were plated in serial dilutions on Luria broth (LB) agar plates. Up to six biopanning rounds were performed Phage Clone Screening Assay and Peptide Sequencing Screening of the phage clones tested for recognition with the CS40 anti-ManLAM mAb was performed by the immuno Dot-Blot technique (Enshell-Seijffers D. et al., *J Mol Biol*, 334, (2003); Enshell-Seijffers and Gershoni, (2002) ibid.]. Briefly, the phage particles were bound directly to nitrocellulose membranes (Schleicher and Schuell GmbH, Dassel, Germany), which were then blocked with TBS/10% skim milk (1 h at RT). The anti-polysaccharide mAb was added (1 µg/ml) to the membranes and incubated overnight at 4° C. The membranes were then washed in TBS 5 times for 5 min at RT. The secondary antibody (HRP-conjugated goat anti-mouse IgG (Jackson Laboratories, West Grove, Pa.) diluted 1:5000 was then added (incubated for 1 h at RT). Positive clones were detected by Dot-Blot. ManLAM was used as a positive binding control. Phage clones that were determined to be positive by the Dot-Blot assay were retested by the same method in triplicate and by ELISA competition. In the selection of the phages with each of the Abs, a control phage clone was selected. These control phage clones did not bind the relevant mAb and did not present amino acids of the motif. The control phages were used as negative controls in binding and immunization assays.

Single-stranded DNA of the positive phage clones was isolated using the QIAprep Spin M13 Kit® (QIAGEN, Hilden, Germany). The DNA sequences encoding the peptide insert were analyzed at the Hebrew University, Jerusalem, Israel by an automated ABI 310 DNA sequencer (Perkin-Elmer, Santa Clara, Calif.). The deduced peptide sequences were aligned by ClustalW alignment using MacVector™ 7.0 (Oxford, UK). The anti-glucuronoxylomannan (GXM) mAb 2H1 was obtained from Prof. Casadaval (Albert Einstein College of Medicine, New York, [Valdon P. and Scharff M. J Immunol Methods. 197:171-9. (1996)]). The anti-MgB sugar mAb 735 was obtained from Prof. Bitter-Suermann (Institute of Medical Microbiology, Hannover, Germany mAb [Kibbelaar R. et al., J Pathol. 159:23-8. (1989)]). ManLAM from *M. tuberculosis* strain H37Rv, PILAM form avirulent mycobacteria, anti-ManLAM mAb (CS40), and anti LAM (CS35) were obtained from Drs. Brennan and Belisle (Colorado State University, Fort Collins, Colo., National Institute of Health grant AI-75320).

Direct Peptide and ManLAM ELISA Assays

Direct ELISA assays were performed by coating 96-well ELISA plates (O/N at 4° C.) with 5-20 µg peptide per well in PBS ManLAM 5 µg/well (50 µl/well). The plates were washed twice in phosphate buffered saline (PBS), blocked with PBS/1% BSA and then washed twice (PBS). Sera diluted in PBS/0.5% BSA (1:50 or 1:200) or CS40 mAb (1:2000) (50 μl per well) was added and incubated for 1 h at 37° C. After washing, alkaline phosphatase-labeled goat anti-mouse immunoglobulin (Sigma, St. Louis, Mo.) was added. Following 90-min incubation at 37° C., p-nitrophenyl phosphate (KPL, Gaithersburg, Md.) was added to the plates, and optical density was measured at 405 nm using ELISA reader (ELX-800UV, Bio-Tec instruments, Winooski, Vt.). In all ELISA procedures, samples were tested in triplicate.

Human sera samples, after appropriate Helsinki endorsement, were obtained from Dr. Rahav (Chaim Sheba Hospital, Ramat Gan, Israel), Dr. Spector (Hadassah University Hospital, Jerusalem, Israel), and Prof. Marchal (Pasteur Institute, Paris).

ELISA Competition

ELISA competition assay was performed as described [Kaur, D., et al. Microbiology 148:3049-3057 (2002)]. Briefly, plates were coated with 0.5 μg/well ManLAM. Plates were blocked as described above. The CS40 mAb (diluted 1:2000) was mixed with various concentrations of either phage particles in TBS/1% BSA ($0-1\times10^{18}$ particles/well) or peptides in PBS/1% BSA (0-200 μg/well). This solution was then transferred to the ELISA plates and incubated for 1 h at 37° C. After washing (PBS), the ELISA procedure was performed as described above. Samples were all tested in triplicate.

Peptide Synthesis and Conjugation

Peptides B11 and A1 were synthesized by a solid-phase technique. For binding assays, peptides corresponding to the phage clones (A1, B11) were synthesized with no additional amino acids. For immunization, the B11 peptide was synthesized with an additional cysteine residue at the amino terminus for conjugation to sulfhydryl-reactive KLH, performed according to manufacturer's instructions (Pierce, Rockford, Ill.).

Peptide synthesis was performed at the Interdepartmental Facility of the Hebrew University Faculty of Medicine, Jerusalem, Israel.

Peptide Immunization

B11 (5 μg and 50 μg) conjugated peptides were administrated to specific pathogen-free (SPF) female BALB/c mice, 5-8 weeks old, intraperitoneally (i.p.) or s.c. The mice were boosted with the same dose three weeks later. In the s.c. immunization route, various adjuvants were tested: KLH-conjugated peptide was emulsified in MPL-TDM adjuvant system (Sigma) or in incomplete Freund's adjuvant (IFA) (Sigma) according to manufacturer's instructions, or in dimethyldioctadecylammonium bromide (DDA) (Fluka, Buchs, Switzerland). Immunization i.p. was performed using the KLH-conjugated peptide emulsified in the MPL-TDM adjuvant system. In all immunization experiments, control groups were immunized with KLH in the relevant adjuvant with no peptide.

In all immunized groups production of Abs was tested in the sera. For this, mice were bled from the tail vein at three times: pre-immunization, two weeks after first administration, and three weeks after second administration. All experiments were performed in accordance with the regulations of the animal experimentation ethics committee of the Hebrew University-Hadassah Medical School.

Experimental *Mycobacterium tuberculosis* Infection

SPF female BALB/c mice were inoculated i.v. in the tail vein with $5\times10^5$ CFU of *M. tuberculosis* strain H37Rv in 200 μl of saline (a kind gift from Prof. G. Marchal, Pasteur Institute, Paris). Thirty days (6 mice) and three months (4 mice) after Mtb infection the mice were bled and tested for the presence of IgG antibodies that bound ManLAM and B11 peptide. Sera from six uninfected mice were used as negative controls. All experiments were performed in accordance with the regulations of the animal experimentation ethics committee of the Hebrew University-Hadassah Medical School.

Peptide Administration

B11 200 μg per mouse per administration was administrated to specific pathogen-free (SPF) female BALB/c mice 5-8 weeks old and to male 4 month old C57BL/6 intraperitoneally (i.p.) or i.n. at various times as described bellow.

All experiments were performed in accordance with the regulations of the animal experimentation ethics committee of the Hebrew University-Hadassah Medical School.

Cell Culture

The cell line RAW 264.7 (ATCC TIB-71) was grown in Dulbecco's modified Eagle's medium (DMEM) supplemented with 10% FCS, 1% penicillin, 1% L-glutamine, 1% nonessential amino acids, and 1% sodium pyruvate (Biological Industries, Beit Haemek, Israel) to an 80% confluent culture at 37° C. in an atmosphere enriched with 5% $CO_2$.

The human monocytic leukemia cell line THP-1 (ATCC 9942) was cultured in RPMI 1640 medium containing Dulbecco's modified Eagle's medium (DMEM) supplemented with 10% FCS, 1% penicillin, 1% L-glutamine, 1% nonessential amino acids, and 1% sodium pyruvate (Biological Industries, Beit Haemek, Israel) grown to $10^6$ cells per ml at 37° C. in an atmosphere enriched with 5% $CO_2$.

LPS Mice Model

Female BALB/c mice, 6-7 weeks old were injected i.p. with 150 μg LPS (Sigma) per mouse. Mice were monitored during a period of 48 hours post injection for illness symptoms as well as general behavior, LPS induced immobility, far tousled or un-tousled, eating, diarrhea or cleaning processes and the like.

Treatment with peptide was performed four days before LPS injection, (i.p. 200 μg peptide per mouse).

Allergic Peritonitis Model

For induction of allergic peritonitis, female BALB/c mice, 5-6 weeks old, were sensitized twice on days 1 and 7 by subcutaneous (s.c.) injection of 0.4 ml of a 0.9% solution of NaCl containing 100 μg ovalbumin (OVA) adsorbed on 1.6 mg $Al(OH)_3$ (all Sigma) the mice received a second dose of the same s.c. injection. On day 11 Peritonitis was induced by the intraperitoneal (i.p.) injection of 0.4 ml of a solution containing 5 μg/ml OVA diluted in saline [Temkin V. et al., *Cytokine*. 24:74-80. (2003)]. Negative control group were sensitized with saline. On day 12 mice were sacrificed (24 h after challenge (peritonitis induction)), and the peritoneal cavity was washed with 5 ml of Tyrode buffer (3 mmol/L potassium chloride, 10 mmol/L sodium hydrogen carbonate, 20 mmol/L sodium chloride, 0.36 mmol/L sodium phosphate, 0.1% glucose (all Sigma)) containing 0.1% gelatin (TG buffer). Peritoneal lavage fluid was centrifuged (5 minutes, 150 g), supernatants were saved for cytokine ELISA, and cell pellets were re-suspended in 2 ml of TG buffer for eosinophil quantification. Cells were stained for 30 min. with Phycoerytrin (PE)-labeled anti-CCR3Ab (0.625 μg/ml; R&D systems, Abingdon, UK) and eosinophils were defined as cells expressing the eotaxin receptor CCR3 [Grimaldi et al., *J Leukoc Biol*. 65:846-53. (1999)] by FACS analysis.

Mice treated with B11 peptide were treated i.p. with 200 μg/mouse 1 hour before sensitizations (Group-S), 1 hour before challenge (Group-C), and 1 hour before both sensitizations and challenge (Group-S+C).

Allergic Asthma Model

For the induction of allergic asthma, mice were sensitized with OVA (Grade V, Sigma) adsorbed to $Al(OH)_3$ gel (Aldrich Chemical Company, Milwaukee, Wis.), using 8 mg OVA/2 ml gel/0.5 ml H$_2$O, pH 7.0-7.5, given intraperitoneally on days 0 and 14. On days 24 and 27 mice were challenged (induction of allergic asthma) with OVA i.n. Negative control group were sensitized with saline. The sensitization and challenge protocol used is an adaptation of a reported procedure [Blyth D. et al., Am. J. Respir. Cell Mol. Biol., 14: 425-438. (1996)].

Twenty-four hours after the second challenge mice were sacrificed. Bronchoalveolar lavage (BAL) was performed with PBS. Eosinophils in Bronchoalveolar lavage fluid (BALF) were detected as described above. Cytokine ELISA was performed to determine cytokine levels in BALF.

Mice treated with B11 peptide were treated with 200 µg/mouse 2 days before sensitizations (Group-S i.p.), 2 days before challenges i.p. (Group-C i.p.), or 1 hour before challenge i.n. (Group-C i.n.) and 2 days both before sensitization and challenge (Group-S+C i.p.).

Lung were excised and examined histologically and photographed after staining with haematoxylin and eosin.

Induction of (TNBS) Colitis.

In Specific pathogen-free male 4 month old C57BL/6 mice lightly anesthetized a 3.5F catheter was carefully inserted into the colon (4 cm proximal to the anus) administering 0.5 mg of the hapten reagent TNBS (Sigma) in 50% ethanol into the lumen of the colon at days 1 and 5. Animals were then kept in a vertical position for 30 and returned to their cages. The mice were monitored for weight loss, behavior, appearance and diarrhea for 11 days. On day 11 mice were sacrificed and tested from macroscopic inflammation symptoms in the spleen, liver and colon [Neurath M. et al., J Exp Med. 182: 1281-90. (1995)].

Mice treated with B11 peptide were treated i.p. with 200 µg/mouse on days 1 and 5.

Cytokine ELISA

Cytokine levels in mouse sera, cell supernatants, peritoneum lavage, and BALF were assessed by ELISA tests using commercial pairs of antibodies and recombinant cytokines for TNFα IFN-γ, IL-10 and IL-4 (Pharmingen International, Oxford, UK), and IL-12 (Biosource International, Camarillo, Calif.) according to the manufacturer's instructions. The ranges of the sensitivities of the ELISA for the murine cytokines were 15-200 pg/ml for TNF-α, IFN-γ, IL-10, and IL-4, and 15-500 pg/ml for IL-12.

Confocal Microscopy of FITC-Labeled B11 Peptide Binding to Raw 264.7 Cell Line

B11 peptide (50 µg) was conjugated to FITC (Biotium, Hayward, Calif.) as described by Sethi et al., [Sethi, K. K., et al. Cell Motil Cytoskeleton 52:231-241 (2002)]. For confocal microscopy, RAW 264.7 cells were grown in 8-well glass slides, Chamber Slide™ (Nunc), as described above. Cells were washed three times in cold PBS and incubated with the FITC-labeled mimotope for 5 min at 4° C. in serial dilutions of 1:2-1:100 in cold PBS. Slides were imaged immediately with a Zeiss 410 confocal laser scanning microscope.

FACS Analysis of FITC-Labeled Mimotope Binding to Cell Lines

RAW 264.7 cells were grown in a 250-ml flask, washed 3 times in cold PBS, and harvested, THP-1 cells were grown to 10$^6$/ml in 250-ml flask, centrifuged at 3000 rpm for 10 min, then washed 3 times in cold PBS. Cells were then incubated for 15 min at 37° C., with the FITC-labeled peptide diluted 1:50, then washed 3 times in cold PBS. The fluorescence levels of 10,000 cell counts were determined by FACS (Becton Dickinson, Franklin Lakes, N.J.) and analyzed by CELLQuest™ software. Assay of competitive binding between D-mannose and the FITC-labeled B11 peptide was performed according to Nguyen and Hildreth [Nguyen, D. G., and Hildreth, J. E. Eur J Immunol 33:483-493 (2003)].

Results

Sequences Selection by Phage Display Technology

All selected phage clones were tested by Dot-Blot for specific binding to anti-ManLAM CS40 mAb. All phage clones bound only to the CS40 mAb and not to three other anti-polysaccharide mAbs: CS35 anti-LAM mAb [Kaur et al. (2002). ibid.], 735 anti-ploy α(2→8) N-acetyl neuraminic acid mAb [Kibbelaar, R. E., et al. *J Pathol* 159:23-28 (1989)], and 2H1 anti-glucuronoxylomannan mAb [Mukherjee; J., et al. *Infect Immun* 60:4534-4541 (1992)].

As is illustrated in the following Table 1, six different phage clones were isolated with mAb CS40. In five of the clones a core motif of 4-5 residues in which a central tryptophan is flanked by hydrophilic amino acids (E/RWS/EXH/K) was observed.

TABLE 1

ManLAM peptide mimotopes

| Clone | Amino acid sequence | |
|-------|---------------------|---|
| A1 | WEADDKNQHGEG | (SEQ ID NO: 6) |
| B11 | ISLTEWSMWYRH | (SEQ ID NO: 1) |
| C1 | EEGPWSTHVGRT | (SEQ ID NO: 2) |
| C3 | WGNEGGDHLQPV | (SEQ ID NO: 3) |
| F7 | SLKIRWELKMYQE | (SEQ ID NO: 4) |
| G3 | AVFRWEKHTWSE | (SEQ ID NO: 5) |

*The postulated motif amino acids are indicated in gray box and bold letters

Binding Properties of the Phage Clones and Synthetic Peptides (B11 and A1)

Efficiency of binding was evaluated by the magnitude of OD decrease when serial dilutions of phage clones were incubated with the CS40 mAb. The phage clones with the higher affinity to mAb showed maximum inhibition of the binding of the mAb to ManLAM with the lowest number of phage particles. When testing the clones that bound the CS40 mAb, two clones, B11 and C1, competed most efficiently with ManLAM (FIG. 1A); 1×10$^{11}$ phage particles per well reduced the OD by 100%. While with clone G3, a similar reduction in the OD was measured, however, it was obtained with 1×10$^{14}$ phage particles per well.

The synthetic B11 peptide bound the CS40 mAb, as tested by direct ELISA, and competed with ManLAM in binding to the mAb, as tested in competitive ELISA (100% decrease in OD with 50 µg/ml of peptide (FIG. 1B). The competitive binding properties were compared to those of a peptide corresponding to the sequence of clone A1. A1 peptide did not compete in the binding of the antibodies vs. ManLAM, thus indicating that the internal aromatic residue and adjacent hydrophilic residues present in the other mimotopes, such as in B11 peptide, are important for the binding to the CS40 mAb.

Antigenic Properties of B11 Phage Clone and Synthetic Peptide

B11 phage clone was tested for the ability to induce ManLAM-binding Abs in sera of immunized mice. Mice (n=5) injected twice with the B11 phage clone developed IgG antibodies specific to ManLAM, compared to naive mice and mice immunized with a control phage, as demonstrated by a serological ELISA test (FIG. 2A).

The antigenic properties of the B11 synthetic peptide was tested for the ability to induce IgM and IgG ManLAM binding Abs. This was performed by immunizing groups of five mice (n=5 per group) with the B11 synthetic peptide conjugated to KLH via an extra cystiene residue at the N-terminus.

Significant levels of IgM Abs, which bound specifically to ManLAM, were detected in mice vaccinated s.c. with 50 µg peptide conjugated to KLH emulsified in the MPL-TDM adjuvant system, two weeks after the first immunization ($p<0.05$ vs. the control groups) (FIG. 2B). In the group vaccinated s.c. with 50 µg peptide conjugated to KLH in MPL TDM, no significant levels of IgG were found after the first immunization. Significant levels ($p<0.05$ vs. the control groups) of specific ManLAM-binding IgG Abs were detected three weeks after the second s.c. immunization (FIG. 2C). The IgGs were mostly of the subtype IgG1 (FIG. 2D). These results were reproduced in three separate experiments. No significant ManLAM-binding antibody levels were detected in any of the other immunized groups (data not shown).

Covalently conjugating the polysaccharide antigen to a carrier protein was used as it improves the immune response by permitting the host to utilize a T-cell dependent immune response [Jacobson, R. M., and Poland, G. A. *Minerva Pediatr* 54:295-303 (2002)].

IgG Antibodies that Bind to the B11 Synthetic Peptide in Mtb-Infected Mice

Figure 3:
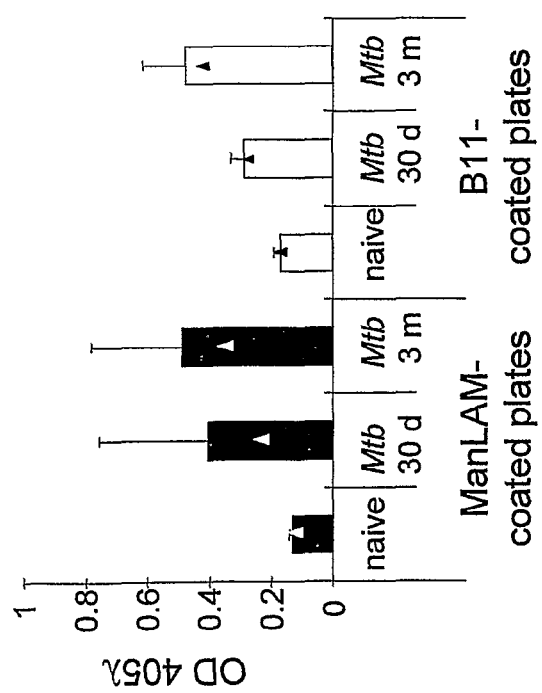
FIG. 3 is a bar graph showing binding of antibodies from sera of 30 days and 3 month Mtb infected mice to ManLAM or B11 mimotope coated plates, as compared to naive mice.

To further investigate if the B11 peptide is a true mimotope of the ManLAM, mice experimentally infected with Mtb that have never been exposed to the peptide were tested for development of antibodies that recognize the B11 peptide, similar to the Abs developed against ManLAM. To this end, thirty days (n=6) and three months (n=4) after an experimental Mtb infection, sera of BALB/c mice were tested for the presence of IgG that recognized ManLAM and B11 peptide, and were compared to naive mice (n=6). In the Mtb-infected mice IgG Abs which binds both ManLAM and B11 peptide were detected, at levels significantly higher than those of the naive mice ($p<0.01$). The antibody levels binding ManLAM as well to B11 peptide were similar (FIG. 3). The same results were obtained when the ELISA assay was performed with or without the extra cysteine at the amino teriminus of the synthetic peptide (data not shown). This gave additional evidence that the peptide with the cysteine (CISLTEWSMWYRH) maintained binding properties to ManLAM-binding antibodies as the original peptide selected (ISLTEWSMWYRH).

IgG Peptide-Binding Antibodies in Human Tuberculosis Patients

Figure 4:
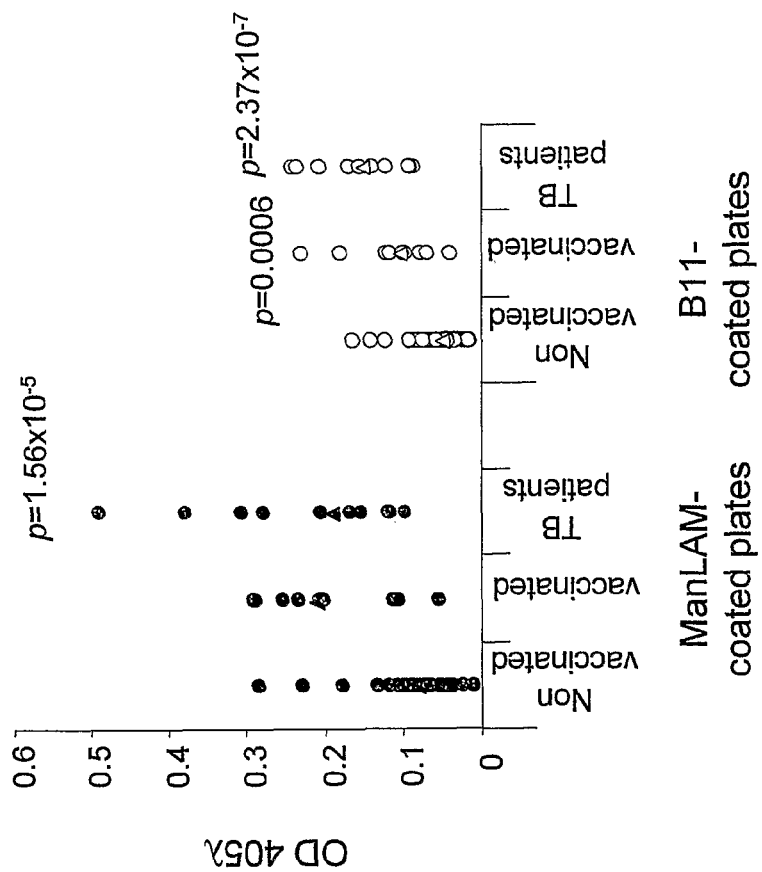
FIG. 4 is a graph showing antibodies in TB human patients' sera binding to ManLAM and the B11 mimotope, compared to non-vaccinated healthy individuals and BCG-vaccinated healthy individuals. Median represented by triangle. The OD presented is the average $OD_{405}$ value of each triplicate sample.

High levels of anti-ManLAM antibodies were measured in tuberculosis (TB) patients [Hamasur, B., et al. *J Microbiol Methods* 45:41-52 (2001)]. The presence of serum antibodies in sera of TB patients that bind the B11 peptide was tested. Significantly higher titers of ManLAM and B11 peptide-binding antibodies in sera of TB patients (n=16) than in sera of healthy individuals (n=36) were found (FIG. 4). Like the antibody levels measured in mice, the human anti-ManLAM and B11 peptide-binding antibody levels were similar, but the variability of the serum titers (SD=0.129 for ManLAM vs. SD=0.058 for the peptide) was smaller when using the B11 peptide as an antigen in the ELISA test (FIG. 4). This might indicate that the peptide can be a more reliable reagent than ManLAM for serological diagnosis. Using ELISA, sera from *Bacillus* Calmette Guerin (BCG)-vaccinated individuals (n=10) was tested, as it is sometimes difficult to distinguish BCG-vaccinated individuals from TB patients [Ciesielski, S. D., *J Fam Pract* 40:76-80 (1995)]. The anti-peptide antibody titers measured in BCG-vaccinated individuals were significantly lower than in TB patients ($p<0.001$) (FIG. 4). Standard deviation (SD) values were smaller in all groups when using the B11 peptide as an antigen compared to the SD values in binding ManLAM as an antigen. SD values of B11 peptide coated plates: Non-vaccinated-SD=0.035, Vaccinated-SD=0.058 TB patients-SD=0.05874. SD values of ManLAM-coated plates: Non-vaccinated-SD=0.057, Vaccinated-SD=0.084, TB-patients-SD=0.129.

B11 Peptide Binds Murine Macrophage Cell Line RAW 264.7 and Human Monocyte Cell Line THP-1

Figure 6:
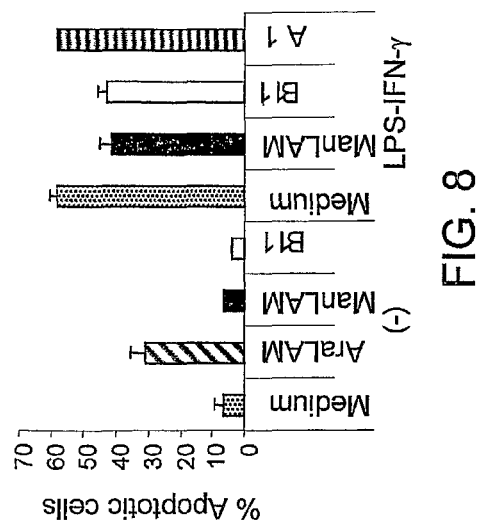
FIG. 6 is a bar graph showing the binding of B11 FITC-labeled peptide to the THP-1 human monocyte cell line and the reduction of binding when 0.125 M D-mannose was added as measured by FACS analysis.

ManLAM binds macrophages and monocytes via mannose-binding receptors [Schlesinger L. et al., *J Immunol*. 152:4070-9. (1994), Nigou J. et al., *J Immunol*. 166:7477-85 (2001), Maeda, N., et al. *J Biol Chem* 278:5513-5516 (2003)]; therefore, the binding of the peptide mimotope of ManLAM to macrophages was examined. Indeed, the FITC-conjugated B11 peptide bound the macrophage cell line RAW 264.7, as seen by confocal microscopy (FIG. 5A) and FACS analysis (FIG. 5B). The binding of the B11 peptide to the macrophages was inhibited by D-mannose, as detected by FACS analysis both in murine RAW 264.7 cell line macrophages (FIG. 5C) and in human THP-1 monocyte cell line (FIG. 6), indicating that the peptide binds a macrophage mannose receptor.

B11 Effects IL-12 Secretion in Murine Macrophage Cell Line Raw 264.7

ManLAM IL-12 secretion in activated macrophage and dendritic cells [Nigou et al., (2001) ibid.]. As expected, in non-activated RAW 264.7 macrophage cell line production IL-12 (FIG. 7) and IL-6 (data not shown) was not induced by the mimotope or ManLAM, whereas PILAM induced high levels (FIG. 7).

Figure 7:
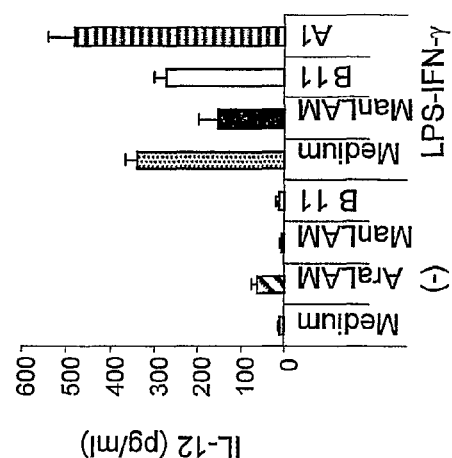
FIG. 7 Is a bar graph showing the effect of B11 peptide on IL-12 secretion in non-activated and LPS-IFN-γ activated RAW 267.4 murine macrophage cell line as measured by cytokine ELISA.

In LPS-IFN-γ-activated RAW 264.7 cells B11 and ManLAM inhibited IL-12 secretion (20% inhibition by the mimotope, 30% inhibition by ManLAM) (FIG. 7). These results show a correlation between the effect of B11 peptide and that of ManLAM that was not detected with the control A1 peptide (Table 1 and FIG. 7).

B11 Mimotope Anti-Apoptotic Features on RAW 264.7 Cell Line

Figure 8:
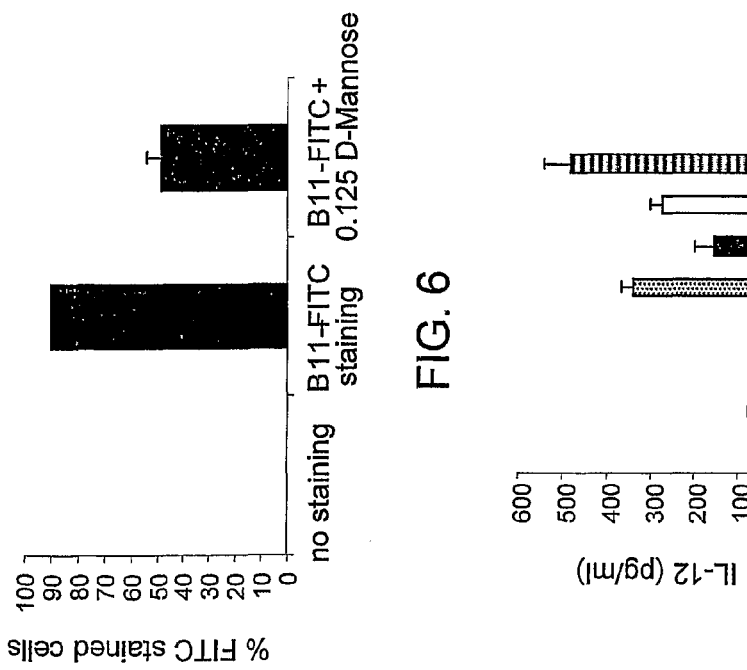
FIG. 8 is a bar graph showing that B11 peptide as ManLAM does not induce apoptosis in non-activated RAW 267.4 murine macrophage cell line and inhibits apoptosis as ManLAM in the LPS-IFNγ activated cells.

ManLAM prevents apoptosis of activated macrophages and dendritic cells [Nigou J. et al., *Microbes Infect*. 4:945-53 (2002)]. In non activated macrophages ManLAM does not affect apoptosis, whereas PILAM increases apoptosis [Dao D., *Infect Immun*. 72:2067-74. (2004)]. Like ManLAM, the B11 peptide did not induce apoptosis (FIG. 8). Further, similar to ManLAM in this assay, in LPS-IFN-γ-activated RAW 264.7 cells, the B11 peptide inhibited apoptosis by 30% (FIG. 8).

B11 Peptide Inhibits Proliferation of Primary Spleen Cells

In vivo proliferation of primary spleen cells was inhibited by B11 peptide, at the concentrations identified in FIGS. 9A-9C. Specifically, proliferation was inhibited by 40-50% in naive (FIG. 9A), Mtb infected (FIG. 9B), and adjuvant stimulated BALB/c mice (FIG. 9C). This was similar to the results obtained with ManLAM in this assay (FIG. 9A-9C).

B11 Peptide Reduced LPS Induced Symptoms in Mice

Mice were injected intra peritoneum (i.p.) with *Escherichia coli* lipopolysaccharide (LPS 150 µg) followed by treatment with B11 peptide (B11 post-treatment). B11 peptide successfully reduced the LPS-induced effects. In a second assay, mice were pre-treated i.p. with 200 µg B11 peptide 4 days before LPS injection the LPS (B11 peptide pre-treatment). These mice exhibited milder LPS symptoms, as determined by the mice appearance, behavior and curing rate. The follow-up observations in both the above assays are summarized in the following Table 1.

TABLE 2

Follow-up on LPS-induced mice non-treated or treated with B11 peptide

| Hr. post LPS injection | State after LPS only | State after LPS-B11 pre-treatment |
|---|---|---|
| 1 hr | healthy | healthy |
| 4 hr | Slower movement<br>Fur tousled and clean<br>Diarrhea<br>Normal breathing | Slower movement<br>Fur slightly tousled and clean<br>No diarrhea<br>Normal breathing |
| 6 hr | LPS induced immobility<br>Fur tousled and clean<br>Diarrhea<br>Heavy breathing | LPS induced immobility<br>Fur tousled and clean<br>No diarrhea<br>Normal breathing |
| 8 hr | LPS induced immobility<br>Fur tousled and clean<br>Heavy breathing<br>Diarrhea | LPS induced immobility<br>Fur tousled and clean<br>Heavy breathing<br>No diarrhea |
| 10 hr | LPS induced immobility<br>Fur tousled and dirty<br>Heavy breathing<br>Diarrhea | LPS induced immobility<br>Fur tousled and clean<br>Heavy breathing<br>No diarrhea |
| 12 hr | LPS induced immobility<br>Fur tousled and dirty<br>Heavy breathing<br>Diarrhea breathing<br>No Diarrhea | LPS induced inmobility<br>50%/50% Fur tousled/normal<br>100% Fur clean<br>50%/50% Heavy/normal |
| 14 hr | LPS induced immobility<br>Fur tousled and dirty<br>Heavy breathing<br>Diarrhea | LPS induced immobility<br>50%/50% Fur slightly tousled/normal<br>100% Clean fur<br>50%/50% Heavy/normal breathing<br>No Diarrhea |
| 20 hr | Slight movement<br>tousled and clean<br>Normal breathing<br>No Diarrhea | Healthy |
| 48 hr | Healthy | Healthy |

The above results show that B11 peptide was effective in ameliorating the symptoms associated with LPS injection, suggesting that this peptide may be a potent therapeutic agent.

B11 Peptide Inhibition of Eosonophils in Allergic Peritonitis

In allergic peritonitis model eosonophils accumulation is induced by OVA injection to BALB/c mice [Temkin V. et al., (2003) ibid]. Specifically, OVA is injected to OVA-sensitized mice resulting in the accumulation of 30% eosonophils in the peritoneum lavage, as compared to no accumulation in mice sensitized with saline only (the control).

In the specific assay, mice were pretreated with 200 μg B11 peptide one hour before challenge with OVA. It was found that eosonophil levels were as in the control group (Saline) (FIG. 10).

These results suggest that B11 peptide was successful in preventing eosonophil accumulation, thereby preventing the development of allergic peritonitis.

Figure 11A:
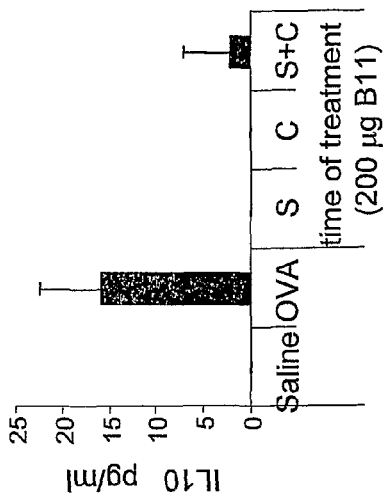
FIG. 11A-11D are bar graphs showing that in an OVA induced allergic peritonitis model, B11-peptide (200 μg per mouse per treatment) effects cytokine levels measured in peritoneum lavage (PLF), compared to the OVA induced mice (TNF-α (FIG. 11A), IFN-γ (FIG. 11B), IL-10 (FIG. 11C), IL-12 (FIG. 11D)), when administered i.p. at different times (S—one hour before OVA sensitization; C—Two days before challenge, S+C—one hour before sensitization and two days before challenge, Saline—are the negative control group sensitized with saline only, OVA—OVA induced allergic peritonitis group un-treated with peptide.
Figure 11B:
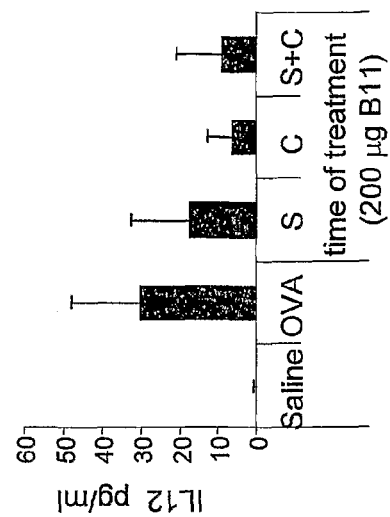
Figure 11C:
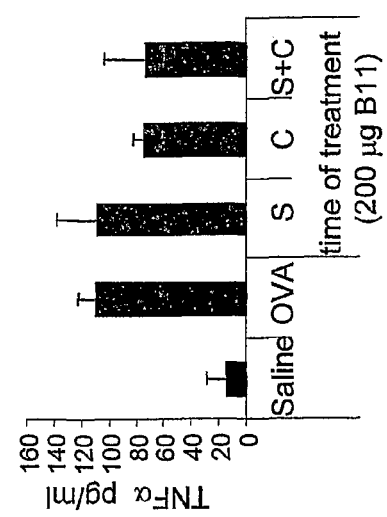
Figure 11D:
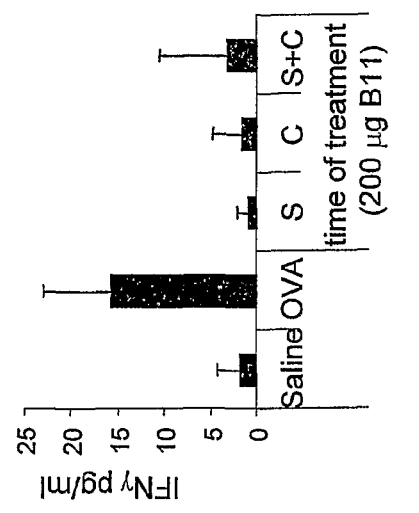

In Allergic Peritonitis Model Induced by OVA in Mice, B11 Peptide Affects Cytokine Secretion in the Peritoneum In the allergic peritonitis model, injection of OVA, to OVA-sensitized mice affects cytokine secretion in the peritoneum. In the specific assay, mice pre-treated with B11 peptide (or with saline in the control group), either 1 hour before sensitization with OVA, with peritonitis induction or by a combination of these two administrations (as described in the M&M). Twenty four hours after induction (challenge) the mice were sacrificed and TNF-α levels were determined. TNF-α levers were found to be significantly lower p<0.05) in the control (Group saline) group than in OVA-sensitized and challenged mice (Group OVA) (FIG. 11A). IFN-γ, IL-10 and IL-12 levels were significantly lower (p<0.05) in all mice treated with B11 peptide (Groups S, C, and S+C) vs. the mice sensitized and challenged with OVA (Group OVA) and similar to the saline sensitized group (Group-Saline) (FIG. 11B-11D). IL-40D levels were significantly lower in all groups treated with B11 vs. the group sensitized and challenged with OVA and similar to the saline sensitized group.

In an Allergic Asthma Model Induced by OVA in Mice, B11 Peptide Reduces Eosonophils Accumulation in the Bronchoalveolar Lavage Fluid (BALF) and in the Lungs In allergic asthma induced by OVA, mice that are sensitized and challenged with OVA, accumulation of ~40% eosonophils is detected in the bronchoalveolar lavage fluid (BALF).

In the present assay in the negative control group (Saline) and in all groups that were treated with B11 peptide at various times and treatments (S i.p., C i.p., S+C i.p. and C i.n.) the eosonophil levels were significantly lower (p<0.05) compared to the OVA sensitized and challenged mice (OVA), as measured by FACS analysis (FIG. 12). In lung histology, no inflammation was observed in the mice treated i.p. with B11 peptide (FIGS. 13C-13D), as in the negative control (FIG. 13A), while in the OVA mice inflammation was observed (FIG. 13B) Mice treatments with 200 μg B11 peptide per treatment were as follows: Group S, inter-peritoneally 2 days before sensitizations; group $C_2$, days before challenges; group S+C treated both before sensitizations and challenges, and intra-nasal one hour before first challenge.

In an Allergic Asthma Model Induced by OVA in Mice, B11 Peptide Affects Cytokine Secretion in the BALF The cytokines IL-4, TNF-α, IL-10 and IL-12 were measured in the BALF of mice treated or not treated with B11 peptide as described above in the OVA induced allergic asthma model.

Figure 14A:
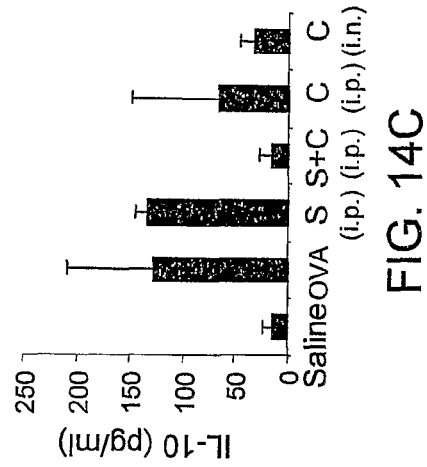
FIG. 14A-14D are bar graphs showing that in an OVA induced allergic asthma model, B11-peptide (200 µg per mouse per treatment) effects cytokine levels measured in BALF, (IL-4 (FIG. 14A), TNF-α (FIG. 14B), IL-10 (FIG. 14C), IL-12 (FIG. 14D)), when administered at different time and treatment schedules: S(i.p.)—two days before sensitizations i.p., C(i.p.).—Two days before challenges i.p., S+C (i.p.)—two days both before sensitization and challenge i.p., C(i.n.)—i.n. one hour before first challenge.
Figure 14B:
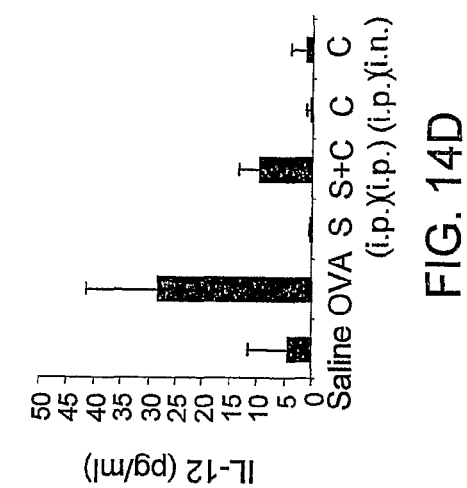
Figure 14C:
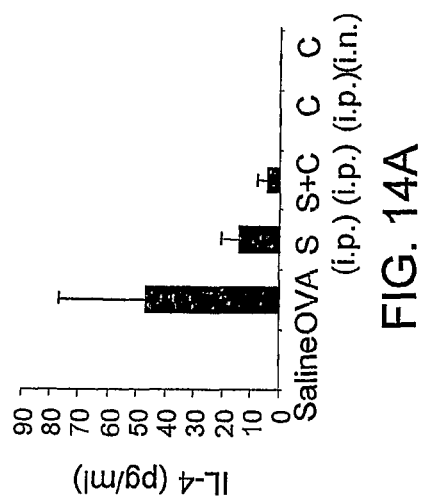
Figure 14D:
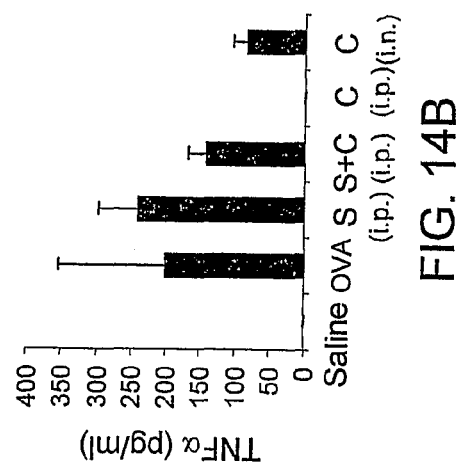

Significant differences in the cytokines levels (as detected by ELISA) was observed in the BALF of mice treated with B11 peptide compared to the non-treated mice (treated with saline). Specifically, cytokine levels were as follows: IL-4 was significantly lower (p<0.05) in the mice treated both i.p. and i.n. before challenge and in the mice treated i.p. both before sensitization and challenge (FIG. 14A). TNF-α was significantly lower p<0.05) in the mice treated twice both i.p. and i.n. before challenge (FIG. 14B). IL-10 was significantly lower (p<0.05) in the mice treated i.n. before challenge and in those treated i.p. both before sensitization and challenge (FIG. 14C). IL-12 was significantly lower (p<0.05) in all mice treated i.p. with the B11 peptide (FIG. 14D).

Treatment with B11 Peptide Reduces Symptoms of Trinitrobenzene Sulfonic Acid (TNBS) Induced Colitis in Mice In C57BL/6 mice induced with Colitis by rectal administration of 0.5% TNBS in ethanol (twice on day 1 and day 5) i.p. administration of 200 μg of B11 peptide twice, at days 1 and 5, reduced the colitis symptoms. In all of the B11 treated mice, normal appearance and behavior, and no diarrhea or weight loss were observed in all 11 days of experiment. On day 11 the macroscopic inflammation symptoms of the colon, spleen and liver of the mice were observed and we noted that these were reduced by the B11 peptide as well. In 75% of the B11 treated mice both spleen and liver appeared normal in size and colorization, and 50% of the colons appeared normal in color, and thickness. None of the colons in the B11 treated mice had lesions.

The invention claimed is:

1. A method of treating a condition selected from the group consisting of multiple sclerosis, Crohn's disease, ulcerative colitis, inflammatory bowel disease, and allergic asthma in a subject having the condition, comprising: administering a therapeutically effective amount of a peptide comprising the amino acid sequence represented by SEQ ID NO: 1 to the subject having the condition.

2. The method according to claim 1, wherein the condition is ulcerative colitis.

* * * * *

SEQUENCE LISTING

<160> NUMBER OF SEQ ID NOS: 6

<210> SEQ ID NO 1
<211> LENGTH: 12
<212> TYPE: PRT
<213> ORGANISM: Artificial sequence
<220> FEATURE:
<223> OTHER INFORMATION: random phage display library

<400> SEQUENCE: 1

Ile Ser Leu Thr Glu Trp Ser Met Trp Tyr Arg His
1               5                   10

<210> SEQ ID NO 2
<211> LENGTH: 12
<212> TYPE: PRT
<213> ORGANISM: Artificial sequence
<220> FEATURE:
<223> OTHER INFORMATION: random phage display library

<400> SEQUENCE: 2

Glu Glu Gly Pro Trp Ser Thr His Val Gly Arg Thr
1               5                   10

<210> SEQ ID NO 3
<211> LENGTH: 12
<212> TYPE: PRT
<213> ORGANISM: Artificial sequence
<220> FEATURE:
<223> OTHER INFORMATION: random phage display library

<400> SEQUENCE: 3

Trp Gly Asn Glu Gly Gly Asp His Leu Gln Pro Val
1               5                   10

<210> SEQ ID NO 4
<211> LENGTH: 13
<212> TYPE: PRT
<213> ORGANISM: Artificial sequence
<220> FEATURE:
<223> OTHER INFORMATION: random phage display library

<400> SEQUENCE: 4

Ser Leu Lys Ile Arg Trp Glu Leu Lys Met Tyr Gln Glu
1               5                   10

<210> SEQ ID NO 5
<211> LENGTH: 12
<212> TYPE: PRT
<213> ORGANISM: Artificial sequence
<220> FEATURE:
<223> OTHER INFORMATION: random phage display library

<400> SEQUENCE: 5

Ala Val Glu Arg Trp Glu Lys His Thr Trp Ser Glu
1               5                   10

<210> SEQ ID NO 6
<211> LENGTH: 12
<212> TYPE: PRT
<213> ORGANISM: Artificial sequence
<220> FEATURE:
<223> OTHER INFORMATION: random phage display library

```
<400> SEQUENCE: 6

Trp Glu Ala Asp Asp Lys Asn Gln His Gly Glu Gly
1               5                   10
```